(12) United States Patent
Tanaka et al.

(10) Patent No.: US 10,280,297 B2
(45) Date of Patent: May 7, 2019

(54) PARTICULATE WATER-ABSORBING AGENT

(71) Applicant: NIPPON SHOKUBAI CO., LTD., Osaka-shi, Osaka (JP)

(72) Inventors: Nobuya Tanaka, Hyogo (JP); Kohei Omori, Hyogo (JP); Kazushi Torii, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/561,173

(22) PCT Filed: Mar. 29, 2016

(86) PCT No.: PCT/JP2016/060179
§ 371 (c)(1),
(2) Date: Sep. 25, 2017

(87) PCT Pub. No.: WO2016/158976
PCT Pub. Date: Oct. 6, 2016

(65) Prior Publication Data
US 2018/0094131 A1    Apr. 5, 2018

(30) Foreign Application Priority Data

Mar. 30, 2015 (JP) .................................. 2015-070173

(51) Int. Cl.
| | |
|---|---|
| *C08L 33/02* | (2006.01) |
| *A41B 13/04* | (2006.01) |
| *A61F 13/15* | (2006.01) |
| *C08J 3/24* | (2006.01) |
| *B01J 20/26* | (2006.01) |
| *B01J 20/28* | (2006.01) |
| *B01J 20/30* | (2006.01) |
| *B01J 20/32* | (2006.01) |

(52) U.S. Cl.
CPC .............. *C08L 33/02* (2013.01); *A41B 13/04* (2013.01); *A61F 13/15* (2013.01); *B01J 20/261* (2013.01); *B01J 20/267* (2013.01); *B01J 20/28004* (2013.01); *B01J 20/28047* (2013.01); *B01J 20/3014* (2013.01); *B01J 20/3021* (2013.01); *B01J 20/3217* (2013.01); *B01J 20/3282* (2013.01); *C08J 3/24* (2013.01); *C08J 3/245* (2013.01); *B01J 2220/68* (2013.01); *C08J 2333/02* (2013.01)

(58) Field of Classification Search
CPC . C08L 33/02; A41B 13/04; B01J 20/26; B01J 20/28; B01J 20/261; B01J 20/267; B01J 20/28004; B01J 2220/68; C08J 3/24; C08J 3/245; C08J 2333/02
USPC ...................................................... 526/317.1
See application file for complete search history.

(56) References Cited

U.S. PATENT DOCUMENTS

| | | | |
|---|---|---|---|
| 4,863,989 A | 9/1989 | Obayashi et al. | |
| 4,972,019 A | 11/1990 | Obayashi et al. | |
| 5,250,530 A * | 10/1993 | Giencke | A01N 43/54 514/217.06 |
| 5,250,630 A * | 10/1993 | Oshima | C08L 13/00 524/432 |
| 5,250,640 A * | 10/1993 | Irie | B01J 19/20 526/88 |
| 5,380,808 A * | 1/1995 | Sumiya | C08F 2/10 526/317.1 |
| 5,610,208 A | 3/1997 | Dairoku et al. | |
| 8,198,209 B2 * | 6/2012 | Torii | A61L 15/18 428/326 |
| 9,180,220 B2 * | 11/2015 | Torii | A61L 15/18 |
| 2002/0120074 A1 | 8/2002 | Wada et al. | |
| 2003/0176589 A1 | 9/2003 | Wada et al. | |
| 2005/0085604 A1 | 4/2005 | Handa et al. | |
| 2005/0272600 A1 | 12/2005 | Wada et al. | |
| 2009/0208748 A1 * | 8/2009 | Torii | A61L 15/60 428/402 |
| 2009/0298685 A1 * | 12/2009 | Torii | A61L 15/18 502/402 |
| 2010/0270501 A1 | 10/2010 | Torii et al. | |
| 2011/0313113 A1 | 12/2011 | Sakamoto et al. | |
| 2012/0211699 A1 | 8/2012 | Daniel et al. | |
| 2012/0267570 A1 | 10/2012 | Shi et al. | |
| 2012/0305842 A1 * | 12/2012 | Torii | A61L 15/18 252/194 |
| 2013/0101851 A1 | 4/2013 | Takaai et al. | |
| 2014/0031473 A1 | 1/2014 | Nogi et al. | |
| 2014/0296465 A1 | 10/2014 | Sakamoto et al. | |
| 2014/0316040 A1 | 10/2014 | Shi et al. | |

FOREIGN PATENT DOCUMENTS

| | | |
|---|---|---|
| EP | 0467073 A1 | 1/1992 |
| EP | 0508810 A2 | 10/1992 |
| EP | 2557095 A1 | 2/2013 |
| JP | 63-118375 | 5/1988 |
| JP | 1-275661 | 11/1989 |
| JP | 4-175319 | 6/1992 |
| JP | 5-112654 | 5/1993 |

(Continued)

OTHER PUBLICATIONS

English Translation of International Preliminary Report on Patentability dated Oct. 12, 2017 issued in International Patent Application No. PCT/JP2016/060179.

(Continued)

*Primary Examiner* — Michael Bernshteyn
(74) *Attorney, Agent, or Firm* — Harness, Dickey & Pierce, P.L.C.

(57) ABSTRACT

The present invention provides a particulate water-absorbing agent which has an excellent fluid retention capacity under pressure and an excellent liquid permeability. Each of the following values of the particulate water-absorbing agent of the present invention falls within a certain range: a ratio represented by "centrifuge retention capacity/Ln (water-soluble component amount)"; a molecular weight distribution of the water-soluble component; a weight average molecular weight after a hydrolysis treatment; and a branching density after the hydrolysis treatment.

10 Claims, 2 Drawing Sheets

(56) References Cited

FOREIGN PATENT DOCUMENTS

| JP | 11-315148 | 11/1999 | | |
|----|-----------|---------|---|---|
| JP | 2003-206305 A | 7/2003 | | |
| JP | 2003-206381 A | 7/2003 | | |
| JP | 2009-531467 A | 9/2009 | | |
| JP | 2011513040 A | 4/2011 | | |
| JP | 2014-512440 A | 5/2014 | | |
| WO | WO-2005/092956 A1 | 10/2005 | | |
| WO | 2007/116778 A1 | 10/2007 | | |
| WO | 2009/110645 A1 | 9/2009 | | |
| WO | WO-2011/040530 A1 | 4/2011 | | |
| WO | WO-2011040530 A1 * | 4/2011 | ............. | B01J 20/26 |
| WO | WO-2011126079 A1 | 10/2011 | | |
| WO | WO-2012/102407 A1 | 8/2012 | | |

OTHER PUBLICATIONS

International Search Report dated Jun. 14, 2016 issued in International Patent Application Patent No. PCT/JP2016/060179.
European Search Report dated Oct. 26, 2018 issued in EP Patent Application No. 16772857.5.
Office Action for Japanese Patent Application No. 2017-510039 dated Nov. 20, 2018 (including ISR and IPRP for PCT/JP2016/060179 previously cited Dec. 27, 2017).

* cited by examiner

PARTICULATE WATER-ABSORBING AGENT

PRIORITY STATEMENT

This patent application is a U.S. national stage filing under 35 U.S.C. § 371 of International Application No. PCT/JP2016/060179 filed 29 Mar. 2016, which claims priority to Japanese Patent Application No. 2015-070173 filed on 30 Mar. 2015. The entire disclosures of each of the above recited applications are incorporated herein by reference.

TECHNICAL FIELD

The present invention relates to a particulate water-absorbing agent.

BACKGROUND ART

Water-absorbing resin (super absorbent polymer or SAP) is a water-swellable, water-insoluble polymer gelling agent. Water-absorbing resin is widely used especially for disposable items, including absorbent articles such as disposable diapers and sanitary napkins, agricultural and horticultural water retaining agents, industrial waterproofing agents and the like. Of such water-absorbing resins, particularly a polyacrylic acid (salt)-based water-absorbing resin, in which acrylic acid and/or a salt thereof are/is used as a monomer(s), is most widely used for industrial purposes from the viewpoint of its high water absorption performance.

Disposable diapers, which are one of the main applications of water-absorbing resin, have undergone advances in terms of performance. These advances created demands for many functions (physical properties) of water-absorbing resin. Specific examples of the physical properties of a water-absorbing resin encompass centrifuge retention capacity, saline flow conductivity, absorption ability under load, and a water-soluble component amount. Therefore, a large number of proposals have been made for surface-crosslinking techniques and for changes of, for example, additives and production processes.

For example, Patent Literature 1 discloses a water-absorbing resin which contains, as a repeating unit of a main chain, a water-soluble unsaturated monomer containing an acrylic acid and/or a salt thereof in an amount of not less than 90 mol % and which has a crosslinked structure therein. The water-absorbing resin has an intrinsic viscosity (IV) which is not more than 7.3 (dL/g) with respect to a weight average molecular weight Log (Mw) of 6.10 after a certain treatment.

It is further demanded that absorption performance not deteriorate for a long period of time during actual use of a disposable diaper. Under the circumstances, techniques for preventing deterioration of a water absorbing agent (i.e. making the water absorbing agent more urine resistant) have been proposed. Examples of such techniques disclosed encompass: a technique in which a metal chelate is added while a method for producing a water-absorbing resin is carried out (Patent Literatures 2 through 5); a technique in which a water-absorbing resin is treated with use of an amine compound having a phosphinic acid group or a phosphonic acid group, or with use of a salt of the amine compound (Patent Literature 6); a technique in which a water-absorbing resin is treated with use of an oxygen-containing reducing inorganic salt (Patent Literature 7); and a technique in which a water-absorbing resin is treated with use of an ion sealing agent such as an aminocarboxylic acid (salt) (Patent Literature 8).

CITATION LIST

Patent Literature

[Patent Literature 1]
Japanese Translation of PCT International Publication, Tokuhyo, No. 2009-531467 (Publication Date: Sep. 3, 2009).
[Patent Literature 2]
Japanese Patent Application Publication, Tokukai, No. 2003-206305 (Publication date: Jul. 22, 2003)
[Patent Literature 3]
Japanese Patent Application Publication, Tokukai, No. 2003-206381 (Publication Date: Jul. 22, 2003)
[Patent Literature 4]
Specification of U.S. Pat. No. 5,610,208 (Registration Date: Mar. 11, 1997).
[Patent Literature 5]
Pamphlet of International Publication No. WO 2005/92956 (Publication Date: Oct. 6, 2005)
[Patent Literature 6]
Japanese Patent Application Publication, Tokukaihei, No. 1-275661 (Publication Date: Nov. 6, 1989)
[Patent Literature 7]
Japanese Patent Application Publication, Tokukaisho, No. 63-118375 (Publication Date: May 23, 1988)
[Patent Literature 8]
Japanese Patent Application Publication, Tokukaihei, No. 11-315148 (Publication Date: Nov. 16, 1999)

SUMMARY OF INVENTION

Technical Problem

However, further improvement of physical properties of a water-absorbing resin (particulate water-absorbing agent) is demanded. For example, conventional techniques such as those described above pose problems with water absorption performance or handleability although the conventional techniques have an excellent property for preventing deterioration of a water absorbing agent (i.e. making the water absorbing agent more urine resistant).

The present invention has been made in view of the problems, and it is an object of the present invention to provide a suitable water-absorbing resin (particulate water-absorbing agent) which has excellent fluid retention capacity under pressure and excellent liquid permeability and which has little absorption performance deterioration in a case where the particulate water-absorbing agent is used for a disposable diaper.

Solution to Problem

As a result of diligent study for attaining the object, the inventors of the present invention found that a water-absorbing resin (particulate water-absorbing agent) has a particularly excellent fluid retention capacity under pressure, a particularly excellent liquid permeability, a particularly excellent water absorption speed, and the like, and an improved urine resistance in a case where the water-absorbing resin is configured so that: the amount of a water-soluble component is small in comparison with a centrifuge retention capacity; a molecular weight distribution of the water-soluble component is narrow, a molecular weight of a polymer chain constituting a main chain of a crosslinked structure falls within a certain range; and a branching density of the polymer chain is low. The inventors of the present invention thus completed the present invention.

Specifically, the present invention includes the following configurations.

A particulate water-absorbing agent containing a polyacrylic acid (salt)-based water-absorbing resin as a main component, the particulate water-absorbing agent satisfying (a) through (d) below:

(a) EXI represented by the following Formula (1) is not less than 11.5:

EXI=centrifuge retention capacity/Ln(water-soluble component amount)   (1), (b) a molecular weight distribution, represented by the following Formula (2), of a water-soluble component is 1.0 to 4.8:

Molecular weight distribution=weight average molecular weight/number average molecular weight   (2), (c) an average molecular weight after a hydrolysis treatment is 450,000 Da to 1,800,000 Da, and (d) a branching density after the hydrolysis treatment is not more than 0.100, the hydrolysis treatment being a treatment carried out by allowing the particulate water-absorbing agent to swell in a 0.9 weight/n % aqueous sodium chloride solution, removing the water-soluble component so as to obtain a gel, and allowing 600 mg of the gel to stand still in 10 mL of a 0.1 N aqueous sodium hydroxide solution at 80° C. for 3 weeks.

Advantageous Effects of Invention

A particulate absorbing agent in accordance with the present invention has not only excellent water absorption performance but also excellent urine resistance in a case where the particulate absorbing agent absorbs urine. Therefore, in a case where the particulate absorbing agent is applied to a sanitary material such as a disposable diaper, in particular, deterioration of the particulate absorbing agent is inhibited. This makes it unlikely for a gel to be deformed during actual use, and therefore allows good water absorption performance to be maintained for a long period of time.

DESCRIPTION OF EMBODIMENTS

Figure 1:
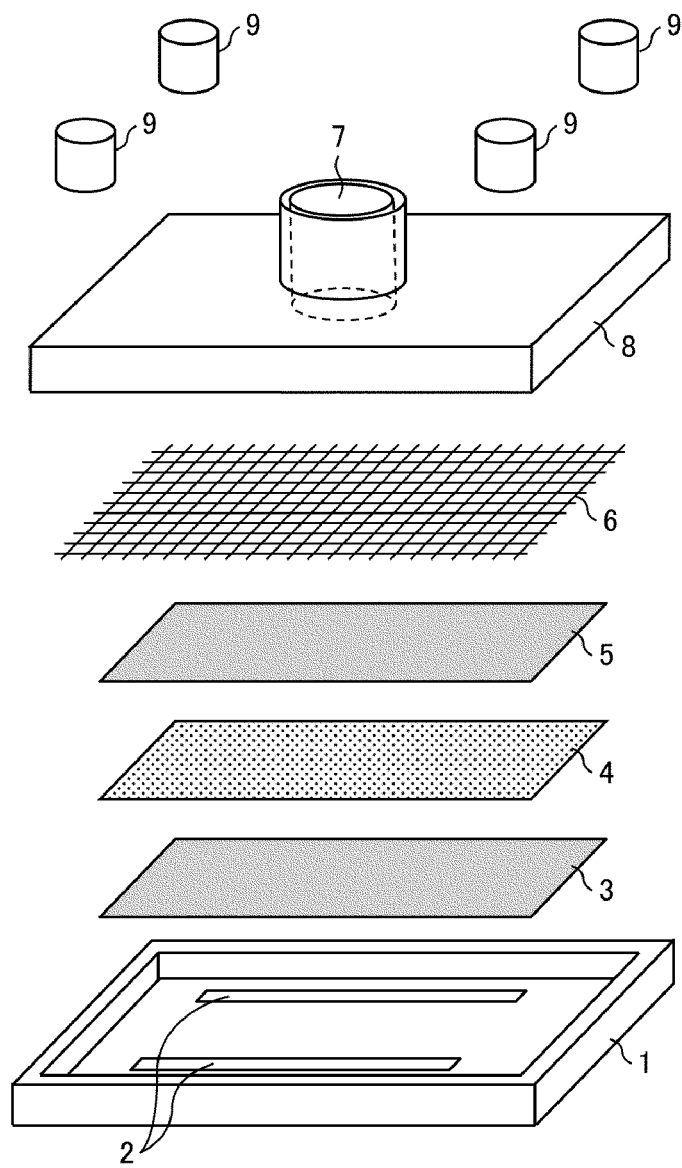
FIG. 1 is a view schematically illustrating a structure of a measuring device used for measuring a diffusion absorbency period.

The following description will discuss a particulate water-absorbing agent in accordance with the present invention in detail. However, the scope of the present invention is not limited to the description, and can be altered from the examples below and practiced as appropriate, provided the object of the present invention is attained.

Specifically, the present invention is not limited to embodiments described below, but can be altered in many ways within the scope of the Claims. An embodiment derived from a proper combination of technical means disclosed in different embodiments is also encompassed in the technical scope of the present invention.

[1] Definitions of Terms

[1-1] "Water-Absorbing Resin"

The term "water-absorbing resin" as used herein means a water-swellable, water-insoluble polymer gelling agent that satisfies the following physical properties. Specifically, the term "water-absorbing resin" as used herein means that a centrifuge retention capacity (CRC), which is prescribed in ERT 441.2-02 as "water-swellability", is not less than 5 g/g, and that a water soluble component (Ext), which is prescribed in ERT 470.2-02 as "water-insolubility", is not more than 50 weight %.

The water-absorbing resin can be designed as appropriate according to its purpose of use, and is not limited to a particular design. The water-absorbing resin is preferably a hydrophilic crosslinked polymer that has been obtained by crosslinking and polymerizing unsaturated monomers each of which has a carboxyl group. Moreover, the water-absorbing resin is not limited to a form in which the water-absorbing resin is wholly (that is, 100 weight %) a polymer, and can be a water-absorbing resin that is surface-crosslinked and/or a composition that contains an additive and the like within a range in which the above-described physical properties (CRC and Ext) are satisfied. Alternatively, the water-absorbing resin can be a water-absorbing resin that varies in shape obtained in each step (examples of the shape of the water-absorbing resin encompass a sheet shape, a fiber shape, a film shape, and a gel shape) or a water-absorbing resin composition that contains an additive and the like.

The water-absorbing resin described herein may refer to not only an end product but also an intermediate produced during a process of producing the water-absorbing resin (e.g. a crosslinked hydrogel polymer after polymerization, a dried polymer after drying, a water-absorbing resin powder before surface crosslinking, or the like). In addition, the water-absorbing resin described herein and the water-absorbing resin composition described above will also be collectively referred to as "water-absorbing resin".

[1-2] "Polyacrylic Acid (Salt)"

The term "polyacrylic acid (salt)" as used herein refers to polyacrylic acid and/or a salt thereof, and refers to a polymer that contains, as a main component, a repeating unit of acrylic acid and/or a salt thereof (hereinafter referred to as "acrylic acid (salt)") and that contains a graft component as an optional component.

The term "main component" means that the acrylic acid (salt) is used (contained) ordinarily in an amount of 50 mol % to 100 mol %, preferably of 70 mol % to 100 mol %, more preferably of 90 mol % to 100 mol %, and even more preferably of substantially 100 mol %, relative to a total amount of monomers for use in polymerization (excluding an internal crosslinking agent).

[1-3] "EDANA" and "ERT"

The term "EDANA" is an acronym for the European Disposables and Nonwovens Associations. The term "ERT" is an acronym for EDANA Recommended Test Methods, which are European standard (de facto international standard) measuring methods for water-absorbing resin. For the present invention, measurements are performed in conformity with the ERT master copy (known Literature: Revised in 2002) unless otherwise specified.

(a) "CRC"

The term "CRC" means a Centrifuge Retention Capacity defined in ERT441.2-02. CRC is also called "fluid retention capacity without pressure". Specifically, the CRC means a fluid retention capacity (unit: g/g) of a water-absorbing resin measured after 0.200 g of a water-absorbing resin contained in a nonwoven fabric bag is immersed in a large excess of a 0.9 weight % aqueous sodium chloride solution for 30 minutes so as to freely swell, and then the water-absorbing resin is drained with use of a centrifugal separator (250 G).

(b) "AAP"

The term "AAP" means an Absorption Against Pressure (fluid retention capacity under pressure) defined in ERT442.2-02. Specifically, "AAP" means a fluid retention capacity (unit: g/g) measured after 0.900 g of a water-absorbing resin has been swollen in a large excess of a 0.9 weight % aqueous sodium chloride solution for 1 hour under a load of 4.83 kPa (0.7 psi). Note that what is meant by the term "Absorption Under Pressure" in ERT442.2-02 is substantially identical with AAP.

(c) "Ext"

The term "Ext" means Extractables (water-soluble component) defined in ERT470.2-02, and refers to a component which is contained in a water-absorbing resin and is soluble in water. Specifically, "Ext" means an amount (unit: weight %) of dissolved polymer measured by pH titration after adding 1.0 g of a water-absorbing resin to 184.3 g of a 0.9 weight % aqueous sodium chloride solution and stirring the resulting mixture at 500 rpm for 16 hours. Note that "Ext" will also be referred to as a water-soluble component amount.

[1-4] "FSR"

The term "FSR" as used herein refers to a Free Swell Rate, and means a rate (unit: g/(g·s)) at which 1 g of a water-absorbing resin absorbs 20 g of 0.9 weight % aqueous sodium chloride solution.

[1-5] "SFC"

The term "SFC" as used herein refers to Saline Flow Conductivity, and means a permeability (unit: $\times 10^{-7} \cdot cm^3 \cdot s \cdot g^{-1}$) of a water-absorbing resin to a 0.69 weight % aqueous sodium chloride solution under a load of 2.07 kPa. A larger SFC value shows a water-absorbing resin having a higher liquid permeability. SFC is measured in conformity with the SFC testing method described in the specification of U.S. Pat. No. 5,669,894.

[1-6] Other

Any range expressed as "X to Y" herein means "not less than X and not more than Y". Unless otherwise specified, "ppm" means "ppm by weight". In addition, "weight" is synonymous with "mass", "weight %" is synonymous with "mass %", and "parts by weight" is synonymous with "parts by mass". Further, " . . . acid (salt)"means" . . . acid and/or salt thereof", and "(meth)acrylic" means "acrylic and/or methacrylic".

The term "urine resistant" as used herein means that a particulate water-absorbing agent has little absorption performance deterioration in a case where the particulate water-absorbing agent absorbs urine. For example, a particulate water-absorbing agent can be deemed urine resistant in a case where a difference between a diffusion absorbency period and a post-deterioration diffusion absorbency period measured by the method described in Examples is small. A difference between a diffusion absorbency period and a post-deterioration diffusion absorbency period in each measurement is preferably not more than 10 seconds. A difference between a combined amount of three diffusion absorbency periods measured and a combined amount of three post-deterioration diffusion absorbency periods measured is preferably not more than 25 seconds, more preferably not more than 20 seconds, and more preferably not more than 15 seconds. In a case where the differences fall within the above ranges, it is possible to maintain good water absorption performance for a long period of time. Therefore, the differences preferably fall within the above ranges.

[2] Physical Properties of Particulate Water-Absorbing Agent

A particulate water-absorbing agent in accordance with the present invention is a particulate water-absorbing agent including a polyacrylic acid (salt)-based water-absorbing resin as a main component, the particulate water-absorbing agent satisfying (a) through (d) below:

(a) EXI represented by the following Formula (1) is not less than 11.5:

$$EXI = \text{centrifuge retention capacity}/\text{Ln(water-soluble component amount)} \quad (1),$$

(b) a molecular weight distribution, represented by the following Formula (2), of a water-soluble component is 1.0 to 4.8:

$$\text{Molecular weight distribution} = \text{weight average molecular weight}/\text{number average molecular weight} \quad (2),$$

(c) a weight average molecular weight after a hydrolysis treatment is 450,000 Da to 1,800,000 Da, and (d) a branching density after the hydrolysis treatment is not more than 0.100.

Physical properties of the particulate water-absorbing agent in accordance with the present invention will be described in detail below.

[2-1] Centrifuge Retention Capacity (CRC)

The particulate water-absorbing agent in accordance with the present invention has a CRC of preferably not less than 23 g/g, more preferably not less than 25 g/g, and even more preferably not less than 26 g/g. An upper limit value of the CRC, which is preferably high, is not particularly limited. However, in view of a balance with other physical properties, the upper limit is preferably not more than 34 g/g, and more preferably not more than 33 g/g. In a case where the CRC is not less than 23 g/g, a large amount of liquid is absorbed by the particulate water-absorbing agent. This allows the particulate water-absorbing agent to be suitable for an absorbent body of an absorbent article such as a disposable diaper. In a case where the CRC is not more than 34 g/g, a rate at which the particulate water-absorbing agent absorbs a body fluid such as urine or blood becomes high. This allows the particulate water-absorbing agent to be suitable for use in a high-speed water absorbing disposable diaper or the like. Note that CRC can be controlled with use of, for example, an internal crosslinking agent and/or a surface-crosslinking agent.

[2-2] Fluid Retention Capacity Under Pressure (AAP)

The particulate water-absorbing agent in accordance with the present invention has an AAP of preferably not less than 20 g/g, more preferably not less than 21 g/g, even more preferably not less than 22 g/g, and particularly preferably not less than 23 g/g. An upper limit value of the AAP, which is preferably high, is not particularly limited. However, in view of a balance with other physical properties, the upper limit is preferably not more than 30 g/g. A particulate water-absorbing agent having an AAP of not less than 20 g/g has little return of a liquid (so-called "re-wet"), which occurs due to a pressure applied to the particulate water-absorbing agent. Therefore, it is preferable that the AAP is not less than 20 g/g. Note that AAP can be controlled, for example, based on a particle size and/or with use of a surface-crosslinking agent.

[2-3] Free Swell Rate (FSR)

The particulate water-absorbing agent in accordance with the present invention has an FSR of preferably not less than 0.28 g/(g·s), more preferably not less than 0.30 g/(g·s), and even more preferably not less than 0.35 g/(g·s). In a case where a particulate water-absorbing agent having an FSR of not less than 0.28 g/(g·s) is used in an absorbent body, a liquid is more sufficiently absorbed. This prevents liquid leakage from occurring. Therefore, it is preferable that the FSR is not less than 0.28 g/(g·s).

[2-4] Water Absorption Time (Vortex)

The particulate water-absorbing agent in accordance with the present invention has Vortex of preferably not more than 42 seconds, more preferably not more than 40 seconds, and even more preferably not more than 35 seconds. In a case where a particulate water-absorbing agent having Vortex of not more than 42 seconds is used in an absorbent body, a liquid is more sufficiently absorbed. This prevents liquid leakage from occurring. Therefore, it is preferable that the Vortex is not more than 42 seconds. The term "water absorption time (Vortex)" as used herein means a water absorption time obtained in conformity with the "Testing Method for Water Absorption Rate of Super Absorbent Polymers" defined in JIS K7224, and refers to a period of time in which 2 g of a particulate water-absorbing agent absorbs 50 g of a physiological saline.

[2-5] Saline Flow Conductivity (SFC)

The particulate water-absorbing agent in accordance with the present invention has an SFC of preferably not less than $10 \times 10^{-7}$ cm$^3$·s·g$^{-1}$, more preferably not less than $20 \times 10^{-7}$ cm$^3$·s·g$^{-1}$, even more preferably not less than $30 \times 10^{-7}$ cm$^3$·s·g$^{-1}$, further still more preferably not less than $50 \times 10^{-7}$ cm$^3$·s·g$^{-1}$, particularly preferably not less than $70 \times 10^{-7}$ cm$^3$·s·g$^{-1}$, and most preferably not less than $90 \times 10^{-7}$ cm$^3$·s·g$^{-1}$. A particulate water-absorbing agent having an SFC of not less than $10 \times 10-7$ cm$^3$·s·g$^{-1}$ has high liquid permeability. Therefore, in a case where a particulate water-absorbing agent having such SFC is used for an absorbent body, the particulate water-absorbing agent has an excellent speed of absorbing liquid. Therefore, it is preferable that the SFC is not less than $10 \times 10^{-7}$ cm$^3$·s·g$^{-1}$.

[2-6] Water-Soluble Component Amount (Ext)

The particulate water-absorbing agent in accordance with the present invention has an Ext of ordinarily not more than 50 weight %, preferably not more than 35 weight %, more preferably not more than 25 weight %, and even more preferably not more than 15 weight %. A lower limit value of the Ext is not particularly limited, but is preferably 0 weight %, and more preferably approximately 0.1 weight %. A water-absorbing agent having an Ext of not more than 50 weight % has a high gel strength and an excellent liquid permeability. In a case where such a particulate water-absorbing agent is used in an absorbent body of an absorbent article such as a disposable diaper, the particulate water-absorbing agent has little return of a liquid (so-called "re-wet"), which occurs due to a pressure applied to the absorbent body. Note that the Ext can be controlled with use of an internal crosslinking agent or the like.

[2-7] EXI

The term "EXI" as used herein is an acronym for "Extractable Index", and means a value obtained by the following Formula (1):

EXI=centrifuge retention capacity/Ln(water-soluble component amount)　　(1), where: the centrifuge retention capacity means CRC defined in ERT441.2-02 as described above; and Ln (water-soluble component amount) means a natural logarithm of the water-soluble component amount.

The particulate water-absorbing agent in accordance with the present invention preferably has a small water-soluble component amount with respect to a centrifuge retention capacity (CRC). The water-soluble component amount can be evaluated by use of EXI. A large EXI shows a small water-soluble component amount with respect to a CRC. A small EXI shows a large water-soluble component amount with respect to a CRC. A large water-soluble component amount may cause a reduction in fluid retention capacity under pressure and in liquid permeability. A large water-soluble component amount, when the particulate water-absorbing agent swells, may also cause a water-soluble component to be eluted. This may inhibit liquid permeation or may cause the occurrence of stickiness.

The particulate water-absorbing agent in accordance with the present invention has an EXI of not less than 11.5, preferably not less than 11.7, and more preferably not less than 12.0. In a case where the EXI is not less than 11.5, it is possible to prevent the reductions in fluid retention capacity under pressure and in liquid permeability described above, and to prevent inhibition of liquid permeation and the occurrence of stickiness.

[2-8] Molecular Weight Distribution of Water-Soluble Component

The term "molecular weight distribution of water-soluble component" herein means a value obtained by the following Formula (2):

Molecular weight distribution=weight average molecular weight/number average molecular weight　　(2).

Note that a weight-average molecular weight, a number average molecular weight, and a molecular weight distribution are herein also referred to as Mw, Mn, and Mw/Mn, respectively.

A molecular weight distribution of a water-soluble component of the particulate water-absorbing agent in accordance with the present invention is 1.0 to 4.8, preferably 2.0 to 4.6, more preferably 2.5 to 4.3, and even more preferably 3.0 to 4.0. Alternatively, the molecular weight distribution can be in any of ranges of 2.0 to 4.8, 2.0 to 4.6, 2.0 to 4.3, and 2.0 to 4.0. The molecular weight distribution is preferably small (theoretically 1.0). However, the molecular weight distribution can fall within the ranges above because the advantageous effect of the present invention can be obtained up to a certain extent of the molecular weight distribution.

Specifically, as an example, a comparison will be made between disposable diapers which use respective particulate absorbing agents having an identical water-soluble component amount and an identical weight average molecular weight of water-soluble components and having different molecular weight distributions. In this case, the particulate absorbing agent having a larger molecular weight distribution contains a larger amount of water-soluble component which have a small molecular weight and which are therefore easily eluted in a short period of time when the particulate absorbing agent swells. This causes physical properties of the particulate absorbing agent having the larger molecular weight to easily deteriorate during use. Therefore, a smaller molecular weight distribution is preferable.

A weight average molecular weight of a water-soluble component of the particulate water-absorbing agent in accordance with the present invention is preferably 200,000 Da to 1,000,000 Da, more preferably 250,000 Da to 1,000, 000 Da, and even more preferably 300,000 Da to 1,000,000 Da. A particulate water-absorbing agent, which has a weight average molecular weight of the water-soluble component of not less than 200,000 Da and which is used for a disposable diaper, has little elution of the water-soluble component in a short period of time. Therefore, the weight average molecular weight is preferably not less than 200,000 Da.

[2-9] Weight Average Molecular Weight after Hydrolysis Treatment

It is difficult from a technical point of view to measure, without any treatment, a molecular weight of a polymer chain which constitutes a main chain having a crosslinked structure. Therefore, for the present invention, a weight average molecular weight is defined by use of a method in which a crosslinked structure is broken by a hydrolysis treatment.

The term "weight average molecular weight after hydrolysis treatment" as used herein means a weight average molecular weight of a polymer contained in an aqueous solution obtained by allowing the particulate water-absorbing agent to swell in a 0.9 weight % aqueous sodium chloride solution, removing a water-soluble component so as to obtain a gel, and allowing 600 mg of the gel to stand still in 10 mL of a 0.1 N aqueous sodium hydroxide solution at 80° C. for 3 weeks.

The particulate water-absorbing agent in accordance with the present invention has a weight average molecular weight of 450,000 Da to 1,800,000 Da, preferably 500,000 Da to 1,800,000 Da, more preferably 550,000 Da to 1,800,000 Da, even more preferably 600,000 Da to 1,800,000 Da, and particularly preferably 650,000 Da to 1,800,000 Da after a hydrolysis treatment. A particulate water-absorbing agent having a weight average molecular weight of not less than 450,000 Da after a hydrolysis treatment allows a plurality of crosslinked structures to be included in a polymer chain constituting a main chain. This causes an increase in absorption capacity under load. Therefore, a weight average molecular weight of not less than 450,000 Da after the hydrolysis treatment is preferable. A particulate water-absorbing agent having a weight average molecular weight of not more than 1,800,000 Da after the hydrolysis treatment prevents a reduction in fluid retention capacity under pressure and liquid permeability which occur due to entanglement of molecular chains. Therefore, a weight average molecular weight of not more than 1,800,000 Da after a hydrolysis treatment is preferable.

[2-10] Branching Density after Hydrolysis Treatment

The term "branching density" as used herein means a value measured as a branching density (Branching Freq.) with use of software "Viscotek OmniSEC 4.6.2" (registered trademark), and shows branching per unit molecule. The term "branching density after hydrolysis treatment" as used herein means a branching density of a polymer contained in an aqueous solution obtained by allowing the particulate water-absorbing agent to swell in a 0.9 weight % aqueous sodium chloride solution, removing a water-soluble component so as to obtain a gel, and allowing 600 mg of the gel to stand still in 10 mL of a 0.1 N aqueous sodium hydroxide solution at 80° C. for 3 weeks. The branching density after a hydrolysis treatment shows a branching density of a polymer which forms a network excluding the water-soluble component, after crosslinking is broken by a hydrolysis treatment.

The particulate water-absorbing agent in accordance with the present invention has a branching density of not more than 0.100, preferably not more than 0.080, more preferably not more than 0.060, even more preferably not more than 0.050, and particularly preferably 0.045 after a hydrolysis treatment. The branching density can be not more than 0.090. A branching density of not more than 0.100 after a hydrolysis treatment allows for a particulate water-absorbing agent which has little branching per unit molecule and which therefore has high fluid retention capacity under pressure and high liquid permeability. Note that the amount of branching of a crosslinked polymer can be made small by causing polymerization of a water-absorbing resin to be uniform.

[2-11] Branching Degree after Hydrolysis Treatment

The term "branching degree after hydrolysis treatment" as used herein means a degree of branching of a polymer contained in an aqueous solution obtained by allowing the particulate water-absorbing agent to swell in a 0.9 weight % aqueous sodium chloride solution, removing a water-soluble component so as to obtain a gel, and allowing 600 mg of the gel to stand still in 10 mL of a 0.1 N aqueous sodium hydroxide solution at 80° C. for 3 weeks. The branching degree after a hydrolysis treatment shows a branching degree of a polymer which forms a network excluding the water-soluble component, after crosslinking is broken by a hydrolysis treatment.

The branching degree is preferably not more than 2.5, more preferably not more than 2.0, even more preferably not more than 1.8, further still more preferably not more than 1.5, particularly preferably not more than 1.3, and most preferably not more than 1.0 after a hydrolysis treatment. The term "branching degree" as used herein means a value measured as a branching degree (Branches) with use of software "Viscotek OmniSEC 4.6.2" (registered trademark).

[2-12] Diffusion Absorbency Period

The term "diffusion absorbency period" as used herein refers to a total amount of time it takes for a particulate water-absorbing agent to absorb a 0.9 weight % aqueous sodium chloride solution in its entirety in a case where the 0.9 weight % aqueous sodium chloride solution is introduced into the particulate water-absorbing agent over a plurality of times.

A diffusion absorbency period can be measured with use of, for example, a diffusion absorbency period measuring device having an appearance schematically illustrated in FIG. 1. FIG. 1 is a view schematically illustrating a structure of the measuring device for use in measurement of a diffusion absorbency period.

To a center part of an acrylic resin tray 1 having internal dimensions of 401 mm (width)×151 mm (length)×30 mm (height) and external dimensions of 411 mm (width)×161 mm (length)×35 mm (height), two strips of double-sided tape (manufactured by Nichiban Co., Ltd.; double-sided tape NICETACK NW-10) 2 each having a width of 10 mm and a length of 300 mm are attached so as to extend along respective corresponding widthwise inner walls and apart from respective widthwise ends by 50 mm. To the double-sided tape 2, a tissue paper 3 that had a thickness of 0.1 mm, a width of 300 mm, and a length of 150 mm is attached so that the tissue paper 3 is not wrinkled. Then, on the tissue paper 3, 13.5 g of a particulate water-absorbing agent 4 is dispersed uniformly (basis weight: 375 g/m$^2$) to an area which has dimension of 300 mm (width)×120 mm (length) and which is 15 mm inward of each widthwise inner wall of the acrylic resin tray 1. Before the dispersing, the wall surface of the acrylic resin tray 1 can be subjected to an antistatic treatment for prevention of static electricity.

Note that a thin nonwoven tissue paper made of pulp is sufficient as the above-described tissue paper. Examples of such a tissue paper encompass Kimwipe manufactured by Nippon Paper Crecia Co., Ltd.

A top sheet 5 is placed on the particulate water-absorbing agent 4. The top sheet 5 is provided apart from each lengthwise inner wall of the acrylic resin tray 1 by an equivalent distance and from each widthwise inner wall the acrylic resin tray 1 by an equivalent distance.

The top sheet 5 is a sheet which is provided so as to be closest to a wearer in an absorbent body such as a disposable diaper worn by the wearer and which contains nonwoven fabric and paper. The top sheet 5 can be a sheet recovered from a conventionally known absorbent body. In Examples, a sheet taken out from a Mamy Poko (product name) tape type (size L, purchased in Japan in June 2014; number on the package bottom surface: 404088043) manufactured by Unicharm Corporation was used. The sheet taken out in each of Examples had a length of 14 cm, a width of 39 cm, and a weight of 3.3 g to 3.6 g, and was used after pulp and the like in the diaper that had adhered to the sheet with an adhesive were sufficiently removed.

A metal gauze 6 (JIS metal gauze; made of stainless steel; 20-mesh) having a width of 390 mm, a length of 90 mm, and a thickness of 0.63 mm is placed on the top sheet 5. Further, an acrylic resin lid 8 (having a width of 400 mm, a length of 150 mm, and a thickness of 20 mm), which has, at a center part thereof, a cylindrical inlet 7 (with a cylindrical part having a height of 100 mm) having an inner diameter of 30 mm, is placed on the metal gauze 6.

Figure 2:
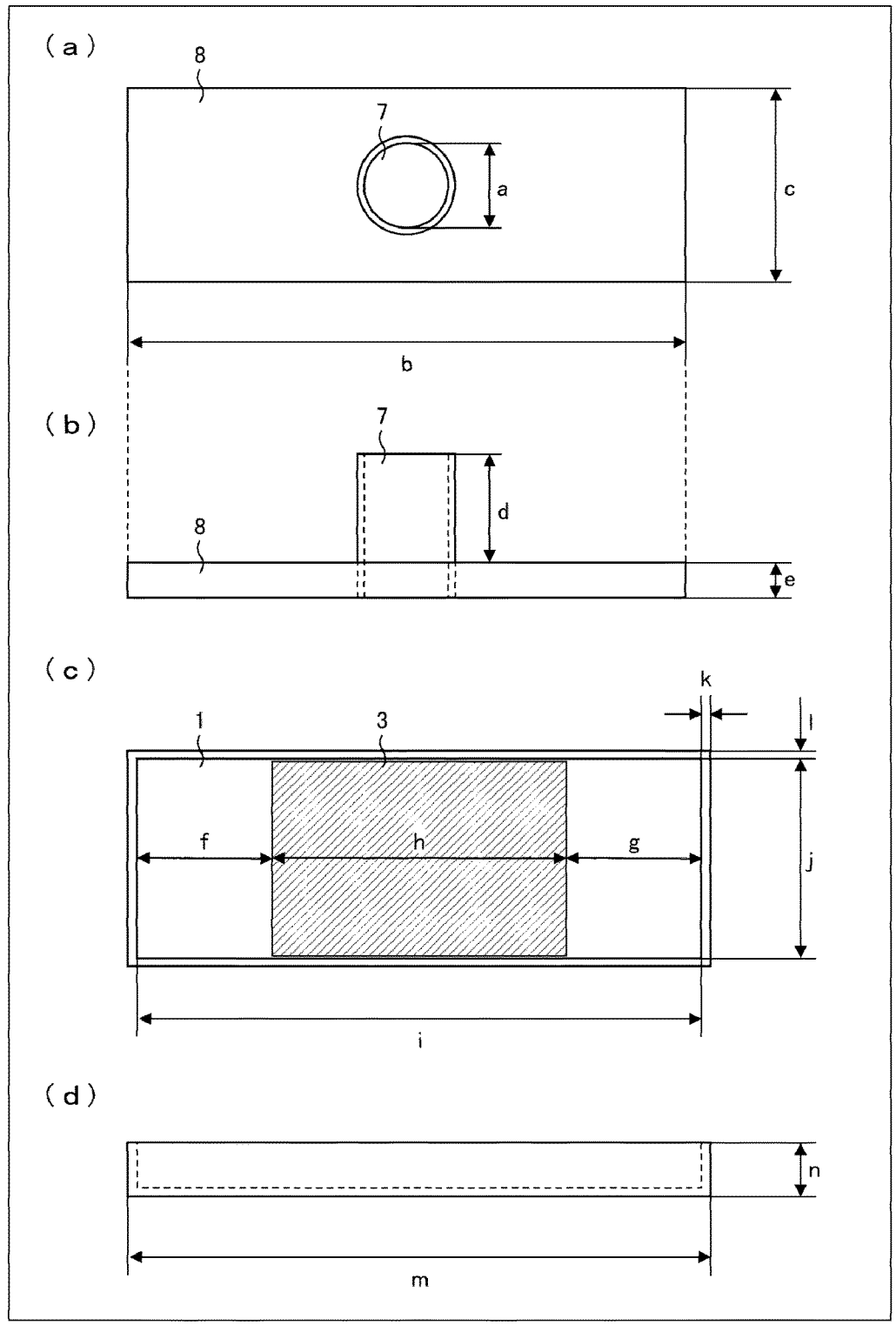
FIG. 2 is a view illustrating an appearance of a lid and a tray of the measuring device used for measuring a diffusion absorbency period.

FIG. 2 is a set of views illustrating respective appearances of a lid and a tray of a measuring device used for measuring a diffusion absorbency period. (a) of FIG. 2 is a top view of the lid. (b) of FIG. 2 is a side view of the lid. (c) of FIG. 2 is a top view of the tray. (d) of FIG. 2 is a side view of the tray.

In (a) of FIG. 2, the symbol "a" indicates the inner diameter of the inlet 7, the symbol "b" indicates the width of the lid 8, and the symbol "c" indicates the length of the lid 8. In (b) of FIG. 2, the symbol "d" indicates the height of the cylindrical part of the inlet 7, and the symbol "e" indicates the thickness of the lid 8.

(c) of FIG. 2 shows how the tissue paper 3 is positioned on the acrylic resin tray 1. In (c) of FIG. 2, the symbols "f" and "g" indicate that the tissue paper 3 is located 50.5 mm away inwardly from the lengthwise inner walls, the symbol "h" indicates the width (300 mm) of the tissue paper 3, the symbol "i" indicates the widthwise internal dimension (401 mm) of the acrylic resin tray 1, the symbol "j" indicates the lengthwise internal dimension (151 mm) of the acrylic resin tray 1 and the length (151 mm) of the tissue paper 3, the symbol "k" indicates the widthwise difference (5 mm) between the internal dimension and external dimension of the acrylic resin tray 1, and the symbol "l" indicates the lengthwise difference (5 mm) between the internal dimension and external dimension of the acrylic resin tray 1.

In (d) of FIG. 2, the symbol "m" indicates the external width (411 mm) of the acrylic resin tray 1, and the symbol "n" indicates the height (35 mm) of the acrylic resin tray 1.

Weights 9 (material: stainless steel) are placed on the lid 8 so that loads are evenly applied to the particulate water-absorbing agent 4. The respective weights and the like of the weights 9 are adjusted so that a total weight of the metal gauze 6, the acrylic resin lid 8, and the weights 9 is 7578 g (a pressure of the loads applied to the area in which the particulate water-absorbing agent is dispersed is 2.07 kPa).

A 0.9 weight % aqueous sodium chloride solution (preferably colored with 0.04 g of blue No. 1 with respect to 1000 g of the aqueous sodium chloride solution) having a temperature adjusted to 37° C.±0.5° C. was introduced over a period of 5 seconds through the inlet 7 into a diffusion absorbency period measuring device in an amount obtained by the following Formula (3):

$$(\text{Weight of particulate water-absorbing agent dispersed} \times \text{AAP} \times (70 \pm 3\%))/3 \quad (3)$$

A first diffusion absorbency period [sec] is a length of time in which the aqueous sodium chloride solution introduced is diffused on the metal gauze 6 while passing through the metal gauze 6, and then absorbed by the particulate water-absorbing agent 4, and then a liquid retained between openings of a mesh is absorbed in its entirety.

The diffusion absorbency period measuring device is placed in a dryer whose temperature is adjusted to 37° C., and is then subjected to heat retention. One hour after the heat retention is started, the aqueous solution is introduced for the second time. A second diffusion absorbency period [sec] is a length of time in which the aqueous solution is introduced for the second time, and then an aqueous solution retained between the openings of the mesh of the metal gauze 6 is absorbed in its entirety. Then, the diffusion absorbency period measuring device is placed in a dryer whose temperature is adjusted to 37° C., and is then subjected to heat retention. One hour after the heat retention is started, the aqueous solution is introduced for the third time. A third diffusion absorbency period [sec] is a length of time in which the aqueous solution is introduced for the third time, and then an aqueous solution retained between the openings of the mesh of the metal gauze 6 is absorbed in its entirety.

[2-13] Post-Deterioration Diffusion Absorbency Period

In measurement of the diffusion absorbency period, a post-deterioration diffusion absorbency period can be measured with use of an aqueous solution obtained by dissolving 0.5 g of L-ascorbic acid in 999.5 g of a 0.9 weight % aqueous sodium chloride solution (preferably colored with 0.04 g of blue No. 1 with respect to 1000 g of the aqueous sodium chloride solution).

[3] Particulate Water-Absorbing Agent Production Method

A method for producing a particulate water-absorbing agent in accordance with the present invention is not limited to any particular one, provided that the particulate water-absorbing agent is obtained. For example, the method is preferably a particulate water-absorbing agent production method including a polymerization step of polymerizing an aqueous solution containing an acrylic acid (salt) as a main component, so as to obtain a crosslinked hydrogel polymer, in the polymerization step, a branching density of the crosslinked hydrogel polymer being controlled. The particulate water-absorbing agent production method allows a particulate water-absorbing agent having the above-described physical properties to be efficiently obtained.

[3-1] Aqueous Monomer Solution Preparing Step

This step is a step of preparing an aqueous solution containing, as a main component, acrylic acid (salt) (this aqueous solution will be hereinafter referred to as "aqueous monomer solution"). It is also possible to use a monomer slurry liquid such that water absorption performance of a particulate water-absorbing agent to be obtained is not degraded. For convenience, however, this section will describe an aqueous monomer solution.

Note that the term "main component" means that the acrylic acid (salt) is used (contained) ordinarily in an amount of not less than 50 mol %, preferably of not less than 70 mol %, and more preferably of not less than 90 mol % (an upper limit being 100 mol %) relative to a total amount of monomers to be used for a polymerization reaction (excluding an internal crosslinking agent).

In the present invention, an acrylic acid and/or an acrylic acid salt (hereinafter referred to as "acrylic acid (salt)") is used as a monomer in view of physical properties of a particulate water-absorbing agent to be obtained and in view of productivity.

The "acrylic acid" can be a publicly known acrylic acid, and can contain, as a polymerization inhibitor, preferably methoxyphenols, and more preferably p-methoxyphenol in an amount of preferably not more than 200 ppm, more preferably 10 ppm to 160 ppm, and even more preferably 20 ppm to 100 ppm in view of polymerizability of the acrylic acid and in view of a color of a particulate water-absorbing agent to be obtained. With regard to an impurity in the acrylic acid, a compound disclosed in U.S. Patent Application Publication No. 2008/0161512 can be applied to the present invention.

The "acrylic acid salt" is obtained by neutralizing the acrylic acid with a basic composition described below. Examples of the acrylic acid salt encompass a commercially available acrylic acid salt (e.g. sodium acrylate) and an acrylic acid salt obtained by neutralizing an acrylic acid in a production plant in which a particulate water-absorbing agent is produced.

In the present invention, the term "basic composition" refers to a composition containing a basic compound, such as a commercially available aqueous sodium hydroxide solution.

Specific examples of the basic compound encompass a carbonate of alkali metal, a bicarbonate of alkali metal, a hydroxide of alkali metal, ammonia, and organic amine. Among these, the basic compound preferably has strong basicity in view of physical properties of a particulate water-absorbing agent to be obtained. That is, the basic compound is preferably a hydroxide of alkali metal, such as sodium hydroxide, potassium hydroxide, or lithium hydroxide, and is more preferably sodium hydroxide.

In the present invention, neutralization can be neutralization of an acrylic acid (before polymerization), neutralization of a crosslinked hydrogel polymer obtained by crosslinking and polymerizing an acrylic acid (after polymerization) (hereinafter referred to as "later neutralization"), or a combination of the neutralization of an acrylic acid and the neutralization of a crosslinked hydrogel polymer obtained by crosslinking and polymerizing an acrylic acid. These neutralizations are not limited to any particular type, and can be of a continuous type or a batch type. Among these, a continuous type is preferable in view of production efficiency and the like.

A temperature during neutralization is not particularly limited, but is preferably 10° C. to 100° C., and more preferably 30° C. to 90° C. Note that with regard to conditions such as a neutralization apparatus and a retention time, the conditions disclosed in European Patent No. 574260 can be applied to the present invention.

A neutralization rate in the present invention is preferably 10 mol % to 100 mol %, more preferably 30 mol % to 95 mol %, even more preferably 45 mol % to 90 mol %, and particularly preferably 60 mol % to 80 mol % per acid group of a monomer. In a case where the neutralization rate is not less than 10 mol %, it is possible to prevent a remarkable reduction in fluid retention capacity. In a case where the neutralization rate is not more than 90 mol %, it is possible to obtain a particulate water-absorbing agent having a high fluid retention capacity under pressure. The neutralization rate also applies to the later neutralization. The neutralization rate can also apply to a neutralization rate for a particulate water-absorbing agent which is an end product.

In the present invention, a particulate water-absorbing agent can be produced by use of an acrylic acid (salt) in combination, as necessary, with a monomer other than the acrylic acid (salt) (hereinafter referred to as "other monomer(s)").

Examples of the other monomer(s) encompass an unsaturated monomer which is water-soluble or hydrophobic. Specifically, the compound disclosed in U.S. Patent Application Publication No. 2005/0215734 (except an acrylic acid) can be applied to the present invention. Note that in a case where the other monomer(s) is used in combination with the acrylic acid (salt), an amount of the other monomer(s) to be used is preferably not more than 30 mol %, and more preferably not more than 10 mol % relative to a total amount of monomers.

The compound disclosed in U.S. Pat. No. 6,241,928 can be suitably used as an internal crosslinking agent for use in the present invention. One of these compounds or two or more of these compounds is/are to be selected in view of reactivity.

In view of water absorption performance and the like of a particulate water-absorbing agent to be obtained, it is preferable to use, as an internal crosslinking agent, preferably a compound having two polymerizable unsaturated groups, and it is more preferable to use a compound having a (poly)alkylene glycol structural unit and two polymerizable unsaturated groups.

In a case of an internal crosslinking agent which has a (poly)alkylene glycol structural unit and has two polymerizable unsaturated groups, a reduction in water solubility is not caused by an increase in hydrophobic group. This allows a uniform polymer network to be formed. Therefore, an improvement in physical properties can be expected.

Preferable examples of the polymerizable unsaturated group encompass an allyl group and a (meth)acrylate group. More preferable examples of the polymerizable unsaturated group encompass a (meth)acrylate group. The (poly)alkylene glycol structural unit is preferably polyethylene glycol. An n number of 2 to 100 is preferable, and an n number of 6 to 50 is more preferable.

Therefore, in the present invention, preferably (poly)alkylene glycol di(meth)acrylate or (poly)alkylene glycol tri(meth)acrylate is to be used, and more preferably (poly)ethylene glycol di(meth)acrylate is to be used.

The internal crosslinking agent is preferably water-soluble, and has a solubility so that preferably not less than 0.1 g and more preferably not less than 1 g of the internal crosslinking agent is dissolved in 100 g of water at 25° C.

The internal crosslinking agent is to be used in an amount of preferably 0.001 mol % to 5 mol %, more preferably 0.002 mol % to 2 mol %, even more preferably 0.04 mol % to 1 mol %, particularly preferably 0.06 mol % to 0.5 mol/n %, and most preferably 0.07 mol % to 0.2 mol % relative to a total amount of monomers. In a case where the amount used falls within the above ranges, a desired particulate water-absorbing agent can be obtained. Note that in a case where the amount used is excessively small, gel strength tends to be lowered and consequently there tends to be an increase in water-soluble component. In a case where the used amount is excessively large, fluid retention capacity tends to be lowered. Therefore, the amount used that is excessively large or excessively small is not preferable.

In the present invention, the following method is preferably used: An aqueous monomer solution, to which a certain amount of internal crosslinking agent has been added in advance, is prepared. Then, the aqueous monomer solution is simultaneously subjected to polymerization and to a crosslinking reaction. Alternatively, other than the above method, examples of a possible method encompass a method in which an internal crosslinking agent is added during or after polymerization, so that postcrosslinking is carried out, a method in which radical crosslinking is carried out with use of a radical polymerization initiator, and a method in which radiation crosslinking is carried out with use of active energy rays such as an electron ray or an ultraviolet ray. Alternatively, these methods can be used in combination.

According to the present invention, any material below can be added to the aqueous monomer solution during the preparation thereof in view of an improvement in physical properties of a particulate water-absorbing agent to be obtained.

Specifically, a hydrophilic polymer such as starch, a starch derivative, cellulose, a cellulose derivative, polyvinyl alcohol, polyacrylic acid (salt), and/or crosslinked polyacrylic acid (salt) can be added in an amount of preferably not more than 50 weight %, more preferably not more than 20 weight %, even more preferably not more than 10 weight %, and particularly preferably not more than 5 weight % (with the lower limit of 0 weight %). A carbonate, an azo compound, a foaming agent such as a gas bubble, a surfactant, a chelating agent, a chain transfer agent, and/or the like can be added in an amount of preferably not more than 5 weight %, more preferably not more than 1 weight %, and even more preferably not more than 0.5 weight % (with the lower limit of 0 weight %).

The above materials can be added to the aqueous monomer solution or can be added during polymerization. Alternatively, the above materials can be added both to the aqueous monomer solution and during polymerization.

In a case where the water-soluble resin or a water-absorbing resin is used as the hydrophilic polymer, a graft polymer or a water-absorbing resin composition (e.g. a polymer produced from starch and an acrylic acid, a polymer produced from PVA and an acrylic acid, and the like) can be obtained. These polymers and water-absorbing resin compositions are also encompassed in the scope of the present invention.

In this step, the above various materials are added during preparation of the aqueous monomer solution. A monomer component concentration in the aqueous monomer solution, although not particularly limited, is preferably 10 weight % to 80 weight %, more preferably 20 weight % to 80 weight %, even more preferably 30 weight % to 70 weight %, and particularly preferably 40 weight % to 60 weight % in view of the physical properties of a particulate water-absorbing agent.

In a case where the form of polymerization employed is aqueous solution polymerization or reversed phase suspension polymerization, solvents other than water can be used in combination as necessary. In such a case, a type of the solvent is not limited to any particular one.

Note that the "monomer component concentration" is a value that can be obtained by the following Formula (4). A weight of an aqueous monomer solution does not include a weight of a graft component, a weight of water-absorbing resin, or a weight of a hydrophobic solvent used in reversed phase suspension polymerization.

Monomer component concentration(weight %)=
(weight of monomer component)/(weight of
aqueous monomer solution)×100       (4).

[3-2] Polymerization Step

This step is a step of polymerizing an aqueous solution whose main component is acrylic acid (salt), so as to obtain a crosslinked hydrogel polymer (herein also referred to as "hydrogel").

In carrying out the polymerization step, the following, for example, can be used: a radical polymerization initiator such as potassium persulfate, ammonium persulfate, sodium persulfate, t-butyl hydroperoxide, hydrogen peroxide, or 2,2'-azobis(2-amidinopropane)dihydrochloride; and an active energy ray such as an ultraviolet ray or an electron ray.

In a case where a radical polymerization initiator is to be used, it is possible to carry out redox polymerization by using, in combination with the radical polymerization initiator, a reducing agent such as sodium sulfite, sodium hydrogen sulfite, ferrous sulfate, or L-ascorbic acid. Preferably, a pyrolytic radical polymerization initiator selected from an azo compound or a peroxide is to be used. The pyrolytic radical polymerization initiator is preferably a water-soluble (preferably not less than 1 g, more preferably not less than 10 g can be dissolved in 100 g of water at 25° C.) polymerization initiator.

The radical polymerization initiator is preferably added to a reaction system in the polymerization step. The "reaction system in the polymerization step" is a reaction system in which polymerization of water-soluble unsaturated monomers may occur, and means a reaction system in which a hydrogel can be produced. Therefore, the "reaction system in the polymerization step" is not limited to any particular configuration, provided that a water-soluble unsaturated monomer is included. The "reaction system in the polymerization step" can include an internal crosslinking agent, a chain transfer agent, α-hydroxycarboxylic acid (salt), or the like.

The radical polymerization initiator is to be added before and/or during the polymerization step, and not after the polymerization step.

Note that the term "before a polymerization step" as used herein means time before polymerization of monomers is started. The term "during a polymerization step" means a period between time at which polymerization of monomers is started and time at which the polymerization ends. The term "after a polymerization step" means time after polymerization of monomers ends.

Whether or not polymerization of monomers has been started can be determined by an increase in temperature of a polymer which is produced by polymerization. Specifically, in a case where the temperature is increased by not less than 3° C. (preferably not less than 5° C.), it is possible to determine that the polymerization of the monomers has been started.

Whether or not polymerization of monomers has ended can be determined by, for example, the fact that an increasing temperature during polymerization reaches a peak and the fact that an amount of residual monomers becomes not more than 5 weight %.

The radical polymerization initiator as described above (particularly a pyrolytic radical polymerization initiator) is to be used in an amount of preferably 0.051 mol % to 1.000 mol %, more preferably 0.054 mol % to 0.2000 mol %, and most preferably 0.058 mol % to 0.1000 mol % relative to a total amount of monomers.

In the polymerization step, it is possible to carry out bulk polymerization, reversed phase suspension polymerization, or precipitation polymerization. In view of performance and ease of control of polymerization, however, it is preferable to carry out aqueous solution polymerization with use of an aqueous monomer solution or an aqueous dispersion solution. These polymerization methods are disclosed, for example, the specification of U.S. Pat. No. 4,625,001, the specification of U.S. Pat. No. 4,769,427, the specification of U.S. Pat. No. 4,873,299, the specification of U.S. Pat. No. 4,093,776, the specification of U.S. Pat. No. 4,367,323, the specification of U.S. Pat. No. 4,446,261, the specification of U.S. Pat. No. 4,683,274, the specification of U.S. Pat. No. 4,690,996, the specification of U.S. Pat. No. 4,721,647, the specification of U.S. Pat. No. 4,738,867, the specification of U.S. Pat. No. 4,748,076, and the specification of U.S. Patent Application Publication No. 2002/40095.

As described above, it is preferable to control a branching density of a crosslinked hydrogel polymer in the polymerization step. Examples of a method for controlling a branching density of a crosslinked hydrogel polymer encompass, but are not particularly limited to: a method in which thin-layer stationary polymerization is carried out with use of an aqueous monomer solution containing a monomer at a high concentration (method 1); and a method in which foaming polymerization is carried out under reduced pressure (method 2).

In the method 1, carrying out thin-layer stationary polymerization with use of a high-concentration aqueous monomer solution makes it easy to control a temperature. This allows a molecular weight of a crosslinked hydrogel polymer to be easily uniform, and therefore makes it possible to more efficiently obtain a particulate water-absorbing agent having the above-described physical properties. A monomer concentration in the aqueous monomer solution is preferably 30 weight % to 60 weight %, more preferably 35 weight % to 55 weight %, and even more preferably 40 weight % to 50 weight %.

The thin-layer stationary polymerization can be carried out while, for example, an aqueous monomer solution is being sandwiched with glass plates. In this case, a distance between the glass plates (i.e. thickness of a layer of the aqueous monomer solution) is preferably 1 mm to 10 mm, more preferably 1 mm to 7 mm, and even more preferably 1 mm to 3 mm. A temperature at which the polymerization is carried out is preferably 40° C. to 70° C., and more preferably 50° C. to 60° C.

In the method 2, carrying out a polymerization step of polymerizing an aqueous monomer solution under reduced pressure makes it easy to remove heat during the polymerization. This allows a molecular weight of a polymer to be easily uniform, and therefore makes it possible to more efficiently obtain a water-absorbing resin powder having the above-described physical properties. In this case, the polymerization step is preferably carried out in a sealed container. A pressure inside the sealed container is preferably not more than 95 kPa, more preferably not more than 90 kPa, more preferably not more than 85 kPa, and particularly preferably not more than 80 kPa. A lower limit value of the pressure is not particularly limited, but is preferably not less than 50 kPa. A monomer concentration in the aqueous monomer solution is preferably 30 weight % to 60 weight %, more preferably 35 weight % to 55 weight %, and even more preferably 40 weight % to 50 weight %.

The present production method preferably further includes steps described below.

[3-3] Gel-Crushing Step

This step is a step of crushing a crosslinked hydrogel polymer during or after the polymerization described above (such a crosslinked hydrogel polymer will be hereinafter referred to as "hydrogel"). By crushing the hydrogel, it is possible to achieve both water absorption speed and liquid permeability.

Examples of a gel-crushing device that can be used in this step encompass, but are not particularly limited to: gel-crushing devices having a plurality of rotational stirring blades such as a batch-type or continuous double-armed kneader; a single-screwed extruder; a twin-screwed extruder; and a meat chopper. Among these gel-crushing devices, a screwed extruder having a porous plate at its tip is preferable. Examples of a screwed extruder having a porous plate at its tip encompass a screwed extruder disclosed in Japanese Patent Application Publication, Tokukai, No. 2000-63527.

[3-4] Drying Step

This step is a step of drying a particulate hydrogel obtained in the gel-crushing step, so as to obtain a dried polymer.

Examples of a drying method employed in the drying step encompass various drying methods such as: heat drying; hot air drying; drying under reduced pressure; infrared drying; microwave drying; drum dryer drying; azeotropic dehydration with a hydrophobic organic solvent; and high humidity drying by use of high temperature water vapor. Among these, hot air drying is preferable. A quantity of air for drying is preferably 0.01 m/sec to 10 m/sec, and more preferably 0.1 m/sec to 5 m/sec.

A drying temperature in the drying step is preferably 100° C. to 250° C., more preferably 130° C. to 220° C., and even more preferably 150° C. to 200° C. In a case where the temperature is not less than 100° C., it is possible to sufficiently change a polymer chain inside a water-absorbing resin. This allows physical properties to be further improved. In a case where the temperature is not more than 250° C., it is possible to prevent damages to a water-absorbing resin. This makes it possible to suppress an increase in water-soluble component amount, and allows physical properties to be further improved. Note that the drying temperature is specified by a temperature of a heating medium. However, in a case where the drying temperature cannot be specified by a temperature of a heating medium such as microwaves, the drying temperature is to be specified by a temperature of a material. The drying temperature can be constant or can be changed within the ranges of temperature described above.

A drying time depends on a surface area of a polymer, a moisture content, and the type of dryer, and is decided so as to adjust the moisture content to a targeted level. The drying time is preferably 10 minutes to 120 minutes, more preferably 20 minutes to 90 minutes, and even more preferably 30 minutes to 60 minutes. In a case where the drying time is not less than 10 minutes, it is possible to sufficiently change a polymer chain inside a water-absorbing resin. This allows physical properties to be further improved. In a case where the drying time is not more than 120 minutes, it is possible to prevent damages to a water-absorbing resin. This makes it possible to suppress an increase in water-soluble component amount, and allows physical properties to be further improved.

In this step, a solid content of a water-absorbing resin after drying (i.e. dried polymer) is preferably not less than 90 weight %, and more preferably not less than 95 weight % (the solid content is measured by a measuring method described later). If the solid content is low, then not only does fluidity worsen so as to interfere with a production process, but there are also disadvantages such as being unable to crush a water-absorbing resin and being unable to particularly control a particle size distribution. Therefore, physical properties may not be improved.

[3-5] Pulverization Step and Classification Step

These steps are steps of pulverizing and classifying a dried polymer, so as to obtain a water-absorbing resin powder. Note that these steps are different from the gel-crushing step described in [3-2] in that a target to be pulverized in these steps has been dried in the drying step. In these steps, a particle size of a water-absorbing resin powder can be controlled to be a certain particle size so as to improve physical properties.

Examples of a pulverizer to be used in the pulverization step encompass, but are not particularly limited to, a roll-type pulverizer such as a roll mill, a hammer-type pulverizer such as a hammer mill, an impact-type pulverizer, a cutter mill, a turbo grinder, a ball mill, and a flash mill. Among these, a roll mill is preferable for controlling a particle size distribution.

In the classification step, any of various sieves and classifiers can be used. Examples of the sieves and classifiers encompass, but are not particularly limited to, vibrating sieves (such as those of an unbalanced weight driving type, a resonance type, a vibrating motor type, an electromagnetic type, or a circular vibrating type), in-plane motion sieves (such as those of a horizontal motion type, a horizontal circular-linear motion type, or a three-dimensional circular motion type), a movable net type sieves, a forced stirring type sieve, a mesh surface vibrating type sieve, a wind power sieve, and a sound wave sieve. Preferably a vibrating sieve or an in-plane motion sieve is used. A mesh size of the sieve is preferably 1000 μm to 300 μm, more preferably 900 μm to 400 μm, and even more preferably 710 μm to 450 μm. In a case where the mesh size falls within these ranges, it is possible to obtain a more preferable particle size distribution for improving physical properties.

A water-absorbing resin powder obtained is generally in the form of primary particles (single particles) or granulated particles, such as a non-uniform pulverized form, a spherical form, a fibrous form, a bar form, a substantially spherical form, or a flat form. Among these, a non-uniform pulverized form is preferable because, for example, the water-absorbing resin powder can be easily fixed in a case where the water-absorbing resin powder is used in an absorbent body.

A water-absorbing resin powder obtained in these steps contain particles having particle diameters of not more than 150 μm at a proportion which is preferably not more than 5 weight %, more preferably not more than 4 weight %, and even more preferably not more than 3 weight %. Note that a particle diameter is herein defined by use of a JIS standard sieve (JIS Z8801-1 (2000)). Note also that "particles having a particle diameter of not more than 150 μm" refers to a water-absorbing resin powder which can pass through a JIS standard sieve having a mesh size of 150 μm.

In a case where particles having particle diameters of not more than 150 μm are contained at a proportion of not more than 5 weight %, it is possible to more reliably prevent, during production of a water-absorbing resin powder, safety and health problems which occur due to scattering of fine particles contained in the water-absorbing resin powder, and it is further possible to inhibit a reduction in physical properties of a particulate water-absorbing agent to be obtained.

In view of improvement of physical properties, a weight average particle diameter (D50) of the water-absorbing resin powder is preferably 200 μm to 600 μm, more preferably 300 μm to 500 μm, even more preferably 320 μm to 480 μm, and particularly preferably 340 μm to 460 μm. In a case where the weight average particle diameter is 200 μm to 600 μm, it is possible to obtain a water-absorbing resin powder having excellent liquid permeability and excellent absorption speed. In a case where such a water-absorbing resin is put to use in, for example, a diaper, it is possible to further suppress, for example, leakage of liquid.

A logarithmic standard deviation ($\sigma\zeta$) of the particle size distribution is preferably 0.20 to 0.50, more preferably 0.25 to 0.45, even more preferably 0.27 to 0.43, and particularly preferably 0.29 to 0.41. In a case where the logarithmic standard deviation ($\sigma\zeta$) of the particle size distribution is 0.20 to 0.50, it is possible to obtain a water-absorbing resin powder having excellent liquid permeability and an excellent speed at which a liquid is absorbed by an absorbent body.

Note that the above particle sizes apply not only to the water-absorbing resin powder but also to a water-absorbing resin after surface crosslinking (hereinafter referred to as "water-absorbing resin particle") and to a particulate water-absorbing agent as an end product. Therefore, it is preferable to carry out surface crosslinking so that the above particle size is maintained, and it is more preferable to carry out particle size adjustment by carrying out a classification step subsequent to a surface-crosslinking step.

[3-6] Surface-Crosslinking Step

This step is a step of causing a part of a surface layer of a water-absorbing resin powder obtained through the above steps (i.e. a part up to several tens of micrometers deep from a surface of the water-absorbing resin powder) to have a higher crosslinking density. This step includes a mixing step, a heating treatment step, and a cooling step.

In a case where a part of a water-absorbing resin in the vicinity of a surface of the water-absorbing resin is crosslinked with use of a surface-crosslinking agent, it is possible to reduce an amount by which a liquid returns due to a pressure applied to a swollen water-absorbing resin. This allows for an increase in AAP and SFC. Consequently, it is possible to obtain an absorbent body which has a small amount of return of a liquid (so-called "re-wet") occurring due to a pressure applied in a case where the water-absorbing resin is used in the absorbent body and which absorbs a liquid at an excellent speed.

(Covalent Bonding Surface-Crosslinking Agent)

Examples of a surface-crosslinking agent used in the present invention encompass, but are not particularly limited to, an organic surface-crosslinking agent and an inorganic surface-crosslinking agent. Among others, an organic surface-crosslinking agent that is reactive with a carboxyl group is preferable in view of the physical properties of a particulate water-absorbing agent and the handleability of the surface-crosslinking agent. Specific examples of the surface-crosslinking agent encompass a polyvalent alcohol compound, an epoxy compound, a polyvalent amine compound or a condensed product of a polyvalent amine compound and a haloepoxy compound, an oxazoline compound, a (mono, di, or poly)oxazolidinone compound, and an alkylene carbonate compound. Among these, it is preferable to use a dehydrative crosslinking agent such as a polyvalent alcohol compound, an alkylene carbonate compound, or an oxazolidinone compound, which needs to react at a high temperature.

Meanwhile, in a case where a dehydrative crosslinking agent is not used, the surface-crosslinking agent is more specifically exemplified by the compounds disclosed in U.S. Pat. Nos. 6,228,930, 6,071,976, 6,254,990, and others. Examples of the surface-crosslinking agent encompass: polyvalent alcohol compounds such as mono-, di-, tri-, tetra-propylene glycol, 1,3-propanediol, glycerin, 1,4-butanediol, 1,3-butanediol, 1,5-pentanediol, 1,6-hexanediol, and sorbitol; epoxy compounds such as ethylene glycol diglycidyl ether and glycidol; alkylene carbonate compounds such as ethylene carbonate; oxetane compounds; and cyclic urea compounds such as 2-imidazolidinone.

An amount of the surface-crosslinking agent to be used is decided as appropriate in ranges of preferably 0.001 parts by weight to 10 parts by weight, and more preferably 0.01 parts by weight to 5 parts by weight, relative to 100 parts by weight of a water-absorbing resin powder. In addition to the surface-crosslinking agent, water is preferably used in combination. An amount of the water to be used is preferably 0.5 parts by weight to 20 parts by weight, and more preferably 0.5 parts by weight to 10 parts by weight, relative to 100 parts by weight of a water-absorbing resin powder. In a case where an inorganic surface-crosslinking agent and an organic surface-crosslinking agent are used in combination, the surface-crosslinking agents are each used in an amount of preferably 0.001 parts by weight to 10 parts by weight, and more preferably 0.01 parts by weight to 5 parts by weight, relative to 100 parts by weight of a water-absorbing resin powder.

In a case where a surface-crosslinking agent or an aqueous solution of a surface-crosslinking agent is mixed with a water-absorbing resin powder, a hydrophilic organic solvent or the like can be used. Examples of the hydrophilic organic solvent to be used encompass: lower alcohols such as methyl alcohol; ketones such as acetone; ethers such as dioxane; amides such as N,N-dimethylformamide; sulfoxides such as dimethyl sulfoxide; and polyvalent alcohols such as ethylene glycol.

An amount of the hydrophilic organic solvent to be used is preferably 0 parts by weight to 10 parts by weight, and more preferably 0 parts by weight to 5 parts by weight, relative to 100 parts by weight of a water-absorbing resin powder. In mixing a crosslinking agent solution with a water-absorbing resin powder, a water-insoluble fine particle powder and/or a surfactant can coexist in an amount not interfering with the effect of the present invention, for example, preferably 0 parts by weight to 10 parts by weight, more preferably 0 parts by weight to 5 parts by weight, and even more preferably 0 parts by weight to 1 part by weight. Examples of a surfactant to be used and an amount of the surfactant are illustrated in U.S. Pat. No. 7,473,739.

Examples of a method for mixing the water-absorbing resin powder and the surface-crosslinking agent encompass, but are not particularly limited to: a method in which a water-absorbing resin powder is immersed in a hydrophilic organic solvent, and then a resultant mixture is mixed with a surface-crosslinking agent which is dissolved in water and/or a hydrophilic organic solvent as necessary; and a method in which a surface-crosslinking agent dissolved in water and/or a hydrophilic organic solvent is mixed directly with a water-absorbing resin powder by spraying or dropping the surface-crosslinking agent.

In mixing the surface-crosslinking agent with the water-absorbing resin powder, a vertical or horizontal high-speed rotation stirring mixer can be suitably used. A rotation rate of the mixer is preferably 100 rpm to 10,000 rpm, and more preferably 300 rpm to 2,000 rpm. Further, the retention time for which the water-absorbing resin powder remains in the mixer is preferably not more than 180 seconds, more preferably 0.1 seconds to 60 seconds, and even more preferably 1 second to 30 seconds.

After the water-absorbing resin powder and the surface-crosslinking agent are mixed, it is ordinarily preferable to complete a crosslinking reaction by carrying out a heating treatment. A heating treatment temperature (temperature of a heating medium), although depending also on a surface-crosslinking agent, is preferably 40° C. to 250° C., and more preferably 150° C. to 250° C. In a case where the heating treatment temperature is not less than 40° C., it is possible to further improve absorption properties such as AAP and SFC. In a case where the heating treatment temperature is not more than 250° C., it is possible to prevent deterioration of a water-absorbing resin powder and deterioration of various physical properties resulting from the deterioration of the water-absorbing resin powder. A heating treatment time is preferably 1 minute to 2 hours, and more preferably 5 minutes to 1 hour.

It is possible to employ, instead of a method in which the surface-crosslinking agent is used, a surface-crosslinking method in which a radical polymerization initiator is used (U.S. Pat. No. 4,783,510 and International Publication No. 2006/062258), or a surface-crosslinking method in which a monomer(s) is polymerized on a surface of a water-absorbing resin (U.S. Patent Application Publication No. 2005/048221, U.S. Patent Application Publication No. 2009/0239966, and International Publication No. 2009/048160).

[3-7] Polyvalent Metal Salt Adding Step

This step is a step of adding a polyvalent metal salt to water-absorbing resin particles obtained through the surface-crosslinking step. In particular, this step is preferably carried out during or after the surface crosslinking. In a case where a polyvalent metal salt (preferably trivalent water-soluble polyvalent metal salt) is added, it is possible to improve SFC without causing AAP of a particulate water-absorbing agent to largely decrease.

In mixing the polyvalent metal salt, it is preferable to mix the polyvalent metal salt as an aqueous solution. A water-soluble polyvalent metal salt concentration in an aqueous solution containing a polyvalent metal salt is preferably not less than 50%, more preferably not less than 60%, even more preferably not less than 70%, particularly preferably not less than 80%, and most preferably not less than 90% relative to a saturating concentration, so as to prevent the polyvalent metal salt from permeating into or being diffused in a water-absorbing resin. Of course, it is possible to use the aqueous solution having a saturating water-soluble polyvalent metal salt concentration. It is also possible that the above hydrophilic organic solvent and/or an organic acid (or a salt thereof) such as a lactic acid (or a salt thereof) coexists in an aqueous solution containing at least a polyvalent metal salt. In such a case, permeation and diffusion of at least a polyvalent metal salt into a water-absorbing resin are inhibited. This allows for improvement in mixability, and is therefore preferable.

Specific examples of the polyvalent metal salt used in this step encompass: sulfate, nitrate, carbonate, phosphate, organic salt, and halide (such as chloride), of metals selected from Zn, Be, Mg, Ca, Sr, Al, Fe, Mn, Ti, Zr, Ce, Ru, Y, Cr, and the like. Examples of the polyvalent metal salt further encompass a polyvalent metal salt disclosed in Japanese Patent Application Publication, Tokukai, No. 2005-11317.

Among the polyvalent metal salts, it is most preferable to use a trivalent water-soluble metal salt. Specific examples of the trivalent water-soluble polyvalent metal salt encompass aluminum chloride, polyaluminum chloride, aluminum sulfate, aluminum nitrate, potassium aluminum sulfate, sodium aluminum sulfate, potassium alum, ammonium alum, sodium alum, sodium aluminate, ferric chloride (III), cerium chloride (III), ruthenium chloride (III), yttrium chloride (III), and chromium chloride (III).

Also in view of solubility of an absorption liquid such as urine, it is preferable to use a salt having these crystallization waters. Aluminum compound is particularly preferable. Examples of a preferable aluminum compound encompass aluminum chloride, polyaluminum chloride, aluminum sulfate, aluminum nitrate, potassium aluminum bis(sulfate), sodium aluminum bis(sulfate), potassium alum, ammonium alum, sodium alum, and sodium aluminate. Among these, aluminum sulfate is particularly preferable. An aqueous solution of aluminum sulfate (preferably a solution whose aluminum sulfate concentration is not less than 90% of a saturating concentration) can be most suitably used. These polyvalent metal salts can be used individually, or two or more of these polyvalent metal salts can be used in combination.

The polyvalent metal salt is to be added in an amount of preferably 0.001% by mass to 5% by mass, and more preferably 0.01% by mass to 1% by mass relative to water-absorbing resin particles.

[4] Application of Particulate Water-Absorbing Agent

A particulate water-absorbing agent in accordance with the present invention has an excellent water absorbent property, and can therefore be used as a water-absorbing water retaining agent for various applications. Examples of applications to which the particulate water-absorbing agent can be put encompass: water-absorbing water retaining agents for absorbent articles such as a disposable diaper, a sanitary napkin, an incontinence pad, and a medical pad; agricultural and horticultural water retaining agents such as a sphagnum replacement, a soil modifying improving agent, a water retaining agent, and an agricultural chemical effect retaining agent; architectural water retaining agents such as an interior wall material condensation preventing agent and a cement additive; a release controlling agent; a refrigerant; a disposable body warmer; a sludge coagulating agent; a food freshness keeping agent; an ion-exchange column material; a dehydrator for sludge or oil; a drying agent; and a humidity controlling material. The particulate water-absorbing agent can be particularly suitably used for hygienic materials for absorption of feces, urine, or blood, such as a disposable diaper or a sanitary napkin.

Alternatively, the particulate water-absorbing agent can be used so as to be contained in an absorbent body. In a case where the absorbent body is used in combination with a proper material, the absorbent body can serve as an absorbent body which is suitable for, for example, an absorbing layer of a hygienic material. In a case where the particulate water-absorbing agent is used in an absorbent body, physical properties of the absorbent body become excellent. This makes it possible to obtain an extremely excellent absorbent body that absorbs a liquid fast and that has a surface layer at which little liquid remains.

The term "absorbent body" refers to a composition that is made of a particulate water-absorbing agent and another material(s) and that is used for an absorbent article, such as a disposable diaper, a sanitary napkin, an incontinence pad, or a medical pad, which absorbs blood, a body fluid, urine, or the like. Examples of the material to be used encompass cellulose fiber. Specific examples of the cellulose fiber encompass: wood pulp fibers such as mechanical pulp made from wood, chemical pulp, semi-chemical pulp, and dissolving pulp; and artificial cellulose fibers such as rayon and acetate. The cellulose fiber is preferably a wood pulp fiber. These cellulose fibers can partially contain a synthetic fiber(s) such as nylon and/or polyester. In a case where the particulate water-absorbing agent is used as a part of an absorbent body, a weight of the particulate water-absorbing agent contained in the absorbent body is preferably not less than 20 weight %, more preferably not less than 30 weight %, even more preferably not less than 40 weight %, and particularly preferably not less than 60 weight %. In a case where a weight of the particulate water-absorbing agent in accordance with the present invention contained in an absorbent body is not less than 20 weight %, the effect of the present invention is more sufficiently obtained. Therefore, such a weight of not less than 20 weight % is preferable.

In order to obtain an absorbent body from the particulate water-absorbing agent and cellulose fibers, a publicly known method for obtaining an absorbent body can be selected as appropriate. Examples of the publicly known method encompass: a method in which the particulate water-absorbing agent is dispersed onto and, as necessary, sandwiched by a paper made of cellulose fibers or a mat made of cellulose fibers; and a method in which cellulose fibers and the particulate water-absorbing agent are uniformly blended. The absorbent body is preferably obtained by a method in which the particulate water-absorbing agent and cellulose fibers are subjected to dry blending, and then a resultant mixture is compressed. This method makes it possible to remarkably suppress an amount of particulate water-absorbing agent falling off from the cellulose fibers. The above resultant mixture is to be compressed preferably while being heated. The heating temperature is, for example, 50° C. to 200° C.

In a case where the absorbent body is used in hygienic materials such as disposable diapers, sanitary napkins, incontinence pads, and medical pads, an absorbent article preferably includes (a) a liquid-permeable top sheet to be positioned so as to be adjacent to a body of a wearer, (b) a liquid-impermeable back sheet to be positioned so as to be far from the body of the wearer and adjacent to the clothes worn by the wearer, and (c) the absorbent body positioned between the top sheet and the back sheet. The absorbent body can be provided in two or more layers or be used in combination with a pulp layer or the like.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

The present invention can be configured as follows:

A particulate water-absorbing agent in accordance with the present invention can be configured so that a weight average molecular weight of a water-soluble component is 200,000 Da to 1,000,000 Da.

The particulate water-absorbing agent in accordance with the present invention can be configured so that a fluid retention capacity under pressure is not less than 20 g/g.

The particulate water-absorbing agent in accordance with the present invention can be configured so that a saline flow conductivity is not less than $10 \times 10^{-7}$ cm$^3$·s·g$^{-1}$.

The particulate water-absorbing agent in accordance with the present invention can be configured so that a water absorption time is not more than 42 seconds.

The particulate water-absorbing agent in accordance with the present invention can be configured so that a free swell rate is not less than 0.28 g/(g·s).

The particulate water-absorbing agent in accordance with the present invention can be configured so that a branching degree after a hydrolysis treatment is not more than 2.5.

The particulate water-absorbing agent in accordance with the present invention can be configured so that the particulate water-absorbing agent is surface-crosslinked with use of a covalent bonding surface-crosslinking agent.

The particulate water-absorbing agent in accordance with the present invention can contain a polyvalent metal salt.

The particulate water-absorbing agent in accordance with the present invention can be configured so that particles having particle diameters of less than 150 μm are contained at a proportion of not more than 5 weight %.

EXAMPLES

The following description will discuss the present invention in more detail with reference to Examples. However, the present invention is not limited to the Examples below.

Properties of a particulate water-absorbing agent were measured by methods described below. Unless otherwise specified, measurements described below are assumed to have been carried out at room temperature (20° C. to 25° C.) and at a humidity of 50 RH %. Unless specified otherwise, a measurement target which was not a particulate water-absorbing agent in the description is to be read as a particulate water-absorbing agent.

<Centrifuge Retention Capacity (CRC)>

A CRC of the particulate water-absorbing agent in accordance with the present invention was measured in conformity with an EDANA method (ERT 441.2-02).

<Fluid Retention Capacity Under Pressure (AAP)>

An AAP of the particulate water-absorbing agent in accordance with the present invention was measured in conformity with an EDANA method (ERT442.2-02). Note that the measurement was carried out under a changed load of 4.83 kPa (0.7 psi).

<Saline Flow Conductivity (SFC)>

An SFC of the particulate water-absorbing agent in accordance with the present invention was measured in conformity with a measuring method disclosed in U.S. Pat. No. 5,669,894.

<Weight Average Particle Diameter (D50) and Logarithmic Standard Deviation (σξ) of Particle Size Distribution>

A weight average particle diameter (D50) and a logarithmic standard deviation (σξ) of a particle size distribution of the particulate water-absorbing agent in accordance with the present invention was measured in conformity with a measuring method disclosed in International Publication No. 2004/69915.

<Proportion of Particles Having Particle Diameters of Less than 150 μm>

A proportion at which particles having particle diameters of less than 150 μm are contained in the particulate water-absorbing agent in accordance with the present invention is obtained by: carrying out a classification step similar to that carried out in a method for measuring the weight average particle diameter (D50) and the logarithmic standard deviation (σξ) of the particle size distribution; and obtaining a proportion (weight %) of particles having sizes with which the particles can pass through a sieve having a mesh size of 150 μm through measuring an amount of the particles that passed the sieve having a mesh size of 150 μm.

<Water-Soluble Component Amount (Ext)>

An Ext of the particulate water-absorbing agent in accordance with the present invention was measured in conformity with an EDANA method (ERT470.2-02).

<Weight Average Molecular Weight (Mw), Number Average Molecular Weight (Mn), Molecular Weight Distribution (Mw/Mn), Branching Degree, and Branching Density after Hydrolysis Treatment>

(Preparation of Sample)

A 200.0 g of a 0.90 weight % aqueous sodium chloride solution was measured and put in a 250-mL plastic container with a lid. Then, 1.00 g of a particulate water-absorbing agent was added to the aqueous solution, and then a resultant mixture was stirred by rotating a stirrer for 16 hours, so that a swollen gel was obtained. The swollen gel was subjected to suction filtration with use of a sheet of filter paper (ADVANTEC Toyo Kaisha Ltd., product name: (JIS P 3801, No. 2) having a thickness of 0.26 mm and a retaining particle diameter of 5 μm, and then a resultant gel was washed by pouring 100.0 g of a 0.90 weight % aqueous sodium chloride solution on the filter paper. The swollen gel was collected in a 250-mL plastic container with a lid, and then 200.0 g of a 0.90 weight % aqueous sodium chloride solution was measured and put in the plastic container. Then, a resultant mixture was stirred by rotating a stirrer for 2 hours, so that a water-soluble component contained in the swollen gel was removed.

(Hydrolysis of swollen gel)

600 mg of the swollen gel washed by the above method and 10 g of a 0.1 mol/L aqueous sodium hydroxide solution (manufactured by Wako Pure Chemical Industries, Ltd., intended for volumetric analysis) were put in a polypropylene test tube (having an inner diameter of 1.8 cm and a length of 15 cm to 18 cm), and then a polypropylene stopper was placed. The test tube was shielded from light, and was then allowed to stand still at 80° C. for 3 weeks. After 3 weeks, a water-absorbing resin was hydrolyzed so as to be in the form of a solution. An insoluble component of the water-absorbing resin after the hydrolysis is ordinarily not more than 5 weight %, preferably not more than 3 weight %, and more preferably 0 weight %. Note that in a case where an insoluble component is more than 5 weight %, the insoluble component of a water-absorbing resin after hydrolysis can be controlled to be in a desired range by adding a 0.1 mol/L aqueous sodium hydroxide solution, extending a period of hydrolysis, or raising, to a high temperature, a temperature at which a test tube stands still.

A resultant solution was 4-fold diluted with use of a solvent described below, and then was allowed to pass through a filter (manufactured by GL Sciences, Inc., GL Chromatodisc, aqueous 25 A, pore size: 0.2 μm). A resultant solution was measured under measurement conditions described below.

(GPC Measurement Conditions)

The measurement was carried out with use of a device, TDA302 (registered trademark) manufactured by VISCOTECH CO., LTD. The device included a size exclusion chromatography, a refractive index detector, a light diffusion detector, and a capillary viscometer.

The measuring device and the measurement conditions were as described below.

Pump/autosampler: GPCmax manufactured by VISCOTECH CO., LTD.

Guard column: OHpak SB-G (manufactured by Showa Denko K.K.)

Column: two OHpak SB-806MHQ (manufactured by Showa Denko K.K.) connected in series Detector: TDA302 manufactured by VISCOTECH CO., LTD. (temperature in the system was maintained at 30° C.)

Solvent: aqueous solution of 60 mM sodium dihydrogen phosphate dihydrate, 20 mM disodium hydrogen phosphate dodecahydrate, and 400 ppm sodium azide (pH of 6.35 to 6.38)

Flow rate: 0.5 mL/min

Pouring amount: 100 μL

Impurities had been sufficiently removed from pure water used in the present measurement. The measurement was carried out while a sufficient amount of solvent was allowed to flow into the device so that a baseline of detection values was stable. In particular, the measurement was carried out while there was no noise peak in the light diffusion detector.

The device was calibrated by use of polyoxyethylene glycol (weight average molecular weight (Mw) 21966, molecular weight distribution (Mw/Mn=1.0), differential refractive index (dn/dc)=0.132, solvent refractive index 1.33) as a standard sample.

In a case where a particulate water-absorbing agent was obtained by polymerizing monomers containing acrylic acid and/or a salt thereof in an amount of not less than 99 mol %, the measurement was carried out assuming that a target polymer to be analyzed had a differential refractive index (dn/dc) of 0.12 and a solvent refractive index of 1.33. In a case where a particulate water-absorbing agent is obtained by copolymerizing more than 1 mol % of monomers other than acrylic acid and/or a salt thereof, it is possible to measure a differential refractive index (dn/dc) in the solvent unique to a polymer of the particulate water-absorbing agent and then to use a numerical value thus measured.

A chart showing the results of the measurement was confirmed, and, in a case where a peak in the results of measuring a light scattering intensity included a large amount of noises, the measurement was carried out again.

The data on the refractive index, the light scattering intensity, and the viscosity were collected and analyzed with use of software "Viscotek OmniSEC 4.6.2" (registered trademark). Based on the refractive index (RI), the light scattering intensity (angle: 7°) LALS, and data obtained from the viscometer (DP), a weight average molecular weight (Mw), a number average molecular weight (Mn), a molecular weight distribution (Mw/Mn), a branching degree (Branches), and a branching density (Branch Freq.) were calculated. Note that for measurement of the branching degree and the branching density, values and a calculation method below were applied to Branching Parameters of the software, and no upper limit value and no lower limit value of molecular weight were specified.

MH Exponent (a): 0.8741

MH Intercept (log K): −4.4152 g/mol

Structure Factor: 0.75

Repeat Factor: 100000

Branching Calculation: Random, polydisperse (tri-functional)

<Weight Average Molecular Weight (Mw), Number Average Molecular Weight (Mn), and Molecular Weight Distribution (Mw/Mn) of Water-Soluble Component>

(Preparation of sample)

A filtrate obtained in <Water-soluble component amount (Ext)>described above was used. In a case where a concentration in a sample was high, the sample was diluted as appropriate with use of a GPC solution so that the concentration would be approximately 0.5 mg/mL.

(Measurement Conditions)

Measurement was carried out under conditions similar to that in which the GPC was measured.

<Free Swell Rate (FSR)>

1.00 g of a particulate water-absorbing agent was put into a 25-mL glass beaker (having a diameter of 32 mm to 34 mm and a height of 50 mm). In so doing, the particulate water-absorbing agent thus put into the beaker was positioned so that a top surface of the particulate water-absorbing agent was horizontal (as necessary, a surface of the particulate water-absorbing agent can be made horizontal by, for example, tapping the beaker with caution).

Then, 20 g of a 0.90 weight % aqueous sodium chloride solution whose temperature was adjusted to 23° C.±0.2° C. was measured and put in a 50-mL glass beaker, and then a total weight (weight W6 [g]) of the aqueous sodium chloride solution and the glass beaker combined was measured. The sodium chloride thus measured was carefully and quickly poured in the 25-mL beaker in which the particulate water-absorbing agent was placed. When the aqueous sodium chloride solution thus poured in came into contact with the particulate water-absorbing agent, time measurement was started. Then, a top surface of the aqueous sodium chloride solution in the beaker into which the aqueous sodium chloride solution had been poured was visually observed at an angle of approximately 200. In so doing, the time measurement was ended (time $t_s$ [s]) when the top surface, which had been a surface of the aqueous sodium chloride solution, was replaced with a surface, of the particulate water-absorbing agent, which had absorbed the aqueous sodium chloride solution as a result of the particulate water-absorbing agent absorbing the aqueous sodium chloride solution.

Next, a weight (weight W7 [g]) of the 50-mL glass beaker, into which the aqueous sodium chloride solution had been poured, was measured. A weight of the poured aqueous sodium chloride solution (weight W8 [g]) and FSR were calculated based on the following Formula (5) and the following Formula (6), respectively:

$$W8[g]=W6-W7 \tag{5}$$

$$FSR[g/(g \cdot s)]=W8/(t_s \times \text{weight}[g] \text{ of particulate water-absorbing agent}) \tag{6}$$

<Water Absorption Time (Vortex)>

A solution was prepared by adding a 0.02 parts by weight of food blue No. 1, which was a food additive, to 1,000 parts by weight of a 0.90 weight % aqueous sodium chloride solution which had been prepared in advance. Then, a temperature of a resultant solution was adjusted to 30° C. (±0.5° C.). 50 mL of the solution was measured and put in a 100-mL beaker. Then, while the inside of the beaker was stirred with use of a cylindrical stirrer (having a length of 40 mm and a thickness of 8 mm) coated with Teflon (registered trademark) at 600 rpm, 2.0 g of a particulate water-absorbing agent obtained in each of Examples and Comparative Examples described later was introduced into the beaker. Then, a water absorption time (seconds) was measured.

A starting point and an ending point of a water absorption time were in conformity with the standard described in JIS K 7224 (1996) "Explanation of Method for Testing Water Absorption Speed of Superabsorbent Resin". A time until the water-absorbing resin absorbed a physiological saline so that the physiological saline being gelled covers (in the form of a V-shape when viewed cross-sectionally) a rotating stirrer tip was measured and evaluated as a water absorption time (seconds).

<Solid Content of Water-Absorbing Resin Powder>

A solid content of a water-absorbing resin powder refers to a percentage which a component that does not volatilize at 180° C. takes up of the water-absorbing resin powder. A relationship between a solid content and a moisture content is as represented by the following Formula (7):

$$\text{Solid content[weight \%]}=100-\text{moisture content [weight \%]} \tag{7}$$

The solid content was measured as described below.

Approximately 1 g of a water-absorbing resin powder (weight $W_1$) was measured and put in an aluminum cup (weight $W_0$) having a bottom surface whose diameter is approximately 5 cm, and was allowed to stand still in a windless dryer at 180° C. for 3 hours so as to be dried. A weight ($W_2$) of the aluminum cup and of the water-absorbing resin powder combined after the drying was measured, and then a solid content was obtained by the following Formula (8):

$$\text{Solid content [weight \%]} = ((W_2 - W_0)/W_1) \times 100 \quad (8)$$

<Diffusion Absorbency Period>

A diffusion absorbency period [sec] was measured by a method described below. The measurement was carried out with use of a diffusion absorbency period measuring device having an appearance schematically illustrated in FIG. 1. FIG. 1 is a view schematically illustrating a structure of the measuring device for use in measurement of a diffusion absorbency period.

To a center part of an acrylic resin tray 1 having internal dimensions of 401 mm (width)×151 mm (length)×30 mm (height) and external dimensions of 411 mm (width)×161 mm (length)×35 mm (height), two strips of double-sided tape (manufactured by Nichiban Co., Ltd.; double-sided tape NICETACK NW-10) 2 each having a width of 10 mm and a length of 300 mm were attached so as to extend along respective corresponding widthwise inner walls and apart from respective widthwise ends by 50 mm. To the double-sided tape 2, a tissue paper 3 which had a thickness of 0.1 mm, a width of 300 mm, and a length of 150 mm (and which was obtained by cutting, to these dimensions, Kimwipe L-100 manufactured by Nippon Paper Crecia Co., Ltd.) was attached so that the tissue paper 3 is not wrinkled. Then, on the tissue paper 3, 13.5 g of a particulate water-absorbing agent 4 was dispersed uniformly (basis weight: 375 g/m²) to an area which had dimension of 300 mm (width)×120 mm (length) and which was 15 mm inward of each widthwise inner wall of the acrylic resin tray 1. Before the dispersing, the wall surface of the acrylic resin tray 1 was subjected to an antistatic treatment for prevention of static electricity.

A top sheet 5 was placed on the particulate water-absorbing agent 4 dispersed. The top sheet 5 was provided apart from each lengthwise inner wall of the acrylic resin tray 1 by an equivalent distance and from each widthwise inner wall the acrylic resin tray 1 by an equivalent distance.

The top sheet 5 was a sheet taken out from a Mamy Poko (product name) tape type (size L, purchased in Japan in June 2014; number on the package bottom surface: 404088043) manufactured by Unicharm Corporation. The sheet taken out had a length of 14 cm, a width of 39 cm, and a weight of 3.3 g to 3.6 g. Pulp and the like in the disposable diaper that had adhered to the sheet with an adhesive were sufficiently removed before the use.

A metal gauze 6 (JIS metal gauze; made of stainless steel; 20-mesh) having a width of 390 mm, a length of 90 mm, and a thickness of 0.63 mm was placed on the top sheet 5. Further, an acrylic resin lid 8 (having a width of 400 mm, a length of 150 mm, and a thickness of 20 mm), which had, at a center part thereof, a cylindrical inlet 7 (with a cylindrical part having a height of 100 mm) having an inner diameter of 30 mm, was placed on the metal gauze 6.

FIG. 2 is a set of views illustrating respective appearances of a lid and a tray of a measuring device used for measuring a diffusion absorbency period. (a) of FIG. 2 is a top view of the lid. (b) of FIG. 2 is a side view of the lid. (c) of FIG. 2 is a top view of the tray. (d) of FIG. 2 is a side view of the tray.

In (a) of FIG. 2, the symbol "a" indicates the inner diameter of the inlet 7, the symbol "b" indicates the width of the lid 8, and the symbol "c" indicates the length of the lid 8. In (b) of FIG. 2, the symbol "d" indicates the height of the cylindrical part of the inlet 7, and the symbol "e" indicates the thickness of the lid 8.

(c) of FIG. 2 shows how the tissue paper 3 is positioned on the acrylic resin tray 1. In (c) of FIG. 2, the symbols "f" and "g" indicate that the tissue paper 3 is located 50.5 mm away inwardly from the lengthwise inner walls, the symbol "h" indicates the width (300 mm) of the tissue paper 3, the symbol "i" indicates the widthwise internal dimension (401 mm) of the acrylic resin tray 1, the symbol "j" indicates the lengthwise internal dimension (151 mm) of the acrylic resin tray 1 and the length (151 mm) of the tissue paper 3, the symbol "k" indicates the widthwise difference (5 mm) between the internal dimension and external dimension of the acrylic resin tray 1, and the symbol "l" indicates the lengthwise difference (5 mm) between the internal dimension and external dimension of the acrylic resin tray 1.

In (d) of FIG. 2, the symbol "m" indicates the external width (411 mm) of the acrylic resin tray 1, and the symbol "n" indicates the height (35 mm) of the acrylic resin tray 1.

Weights 9 (material: stainless steel) were placed on the lid 8 so that loads were evenly applied to the particulate water-absorbing agent 4. The respective weights and the like of the weights 9 were adjusted so that a total weight of the metal gauze 6, the acrylic resin lid 8, and the weights 9 was 7578 g (a pressure of the loads applied to the area in which the particulate water-absorbing agent was dispersed was 2.07 kPa).

75 g of a 0.9 weight % aqueous sodium chloride solution (preferably colored with 0.04 g of blue No. 1 with respect to 1000 g of the aqueous sodium chloride solution) having a temperature adjusted to 37° C.±0.5° C. was introduced over a period of 5 seconds through the inlet 7 into a diffusion absorbency period measuring device. The aqueous sodium chloride solution introduced was diffused on the metal gauze 6 while passing through the metal gauze 6, and was then absorbed by the particulate water-absorbing agent 4. A time until a liquid retained between openings of a mesh was absorbed in its entirety was decided as a first diffusion absorbency period [sec].

The diffusion absorbency period measuring device was placed in a dryer whose temperature was adjusted to 37° C., and was then subjected to heat retention. One hour after the heat retention was started, the aqueous solution was introduced for the second time. A second diffusion absorbency period [sec] decided was a length of time in which the aqueous solution was introduced for second time, and then an aqueous solution retained between the openings of the mesh of the metal gauze 6 was absorbed in its entirety. Then, the diffusion absorbency period measuring device was placed in a dryer whose temperature is adjusted to 37° C., and was then subjected to heat retention. One hour after the heat retention was started, the aqueous solution was introduced for the third time. A third diffusion absorbency period [sec] decided was a length of time in which the aqueous solution was introduced for third time, and then an aqueous solution retained between the openings of the mesh of the metal gauze 6 was absorbed in its entirety.

<Post-Deterioration Diffusion Absorbency Period>

A post-deterioration diffusion absorbency period was measured, as with the measurement of the diffusion absorbency period, with use of an aqueous solution obtained by dissolving 0.5 g of L-ascorbic acid in 999.5 g of a 0.9 weight % aqueous sodium chloride solution (preferably colored with 0.04 g of blue No. 1 with respect to 1000 g of the aqueous sodium chloride solution).

Example 1

23.2 g of acrylic acid, 0.135 g of polyethyleneglycol diacrylate (weight average molecular weight (Mw) 523 Da) (0.080 mol % with respect to the acrylic acid), 0.071 g of a 2.0 weight % aqueous trisodium diethylenetriamine pentaacetate solution, 22.2 g of ion exchange water, and 9.6 g of a 48.5 weight % aqueous sodium hydroxide solution were mixed in a 120-mL polypropylene container having an inner diameter of 50 mm, so that a solution (A) was prepared.

While the solution (A) was being stirred with use of a magnetic stirrer, 9.8 g of a 48.5 weight % aqueous sodium hydroxide solution was added in an open system over a period of approximately 5 seconds to the solution (A) whose temperature was adjusted to 45° C. and then was mixed with the solution (A), so that an aqueous monomer solution (1) was prepared. Note that a temperature of the aqueous monomer solution (1) increased to approximately 80° C. due to heat of neutralization and heat of dissolution which were generated during the mixing.

Then, when the temperature of the resultant aqueous monomer solution (1) reached 78° C., 1.01 g of a 4.5 weight % aqueous sodium persulfate solution was added, and a resultant mixture was stirred for approximately 3 seconds. Then, a resultant reaction liquid (1) was poured into a stainless steel petri dish in an open system.

The stainless steel petri dish had an inner diameter of 88 mm and a height of 20 mm. Note that a surface temperature of the stainless steel petri dish was heated to 50° C. in advance with use of a hot plate (NEO HOTPLATE Hi-1000 manufactured by Iuchi Seiei Do Ltd.)

After the reaction liquid (1) was supplied, the stainless steel petri dish was quickly covered with a glass container having an air outlet. Then, air inside the case was sucked with use of a vacuum pump so that a pressure inside the case would be 85 kPa. Note that a pressure outside the case was 101.3 kPa (normal pressure).

A while after the reaction liquid (1) was poured into the stainless steel petri dish, polymerization was started. The polymerization proceeded while water vapor was being generated and the mixture was swelling and foaming in various upward directions. Then, a mixture was shrunk to a size slightly larger than a bottom surface of the stainless steel petri dish. This swelling and shrinkage of the mixture ended within approximately 1 minute. After the mixture was kept in the polymerization container (i.e. the stainless steel petri dish covered with the glass container) for 3 minutes, a crosslinked hydrogel polymer (hereinafter referred to as "hydrogel") (1) was taken out.

The hydrogel (1) thus obtained was subjected to gel-crushing with use of a screw extruder (meat chopper) having specifications below. The screw extruder included a porous plate at a tip thereof. The porous plate had a diameter of 82 mm and a pore size of 8.0 mm. The number of pores of the porous plate was 33. The porous plate had a thickness of 9.5 mm. The gel-crushing was carried out while the hydrogel (1) was being introduced in an amount of approximately 360 g/min and deionized water at 90° C. was being added in an amount of 50 g/min.

The hydrogel (1) subjected to the gel-crushing was spread on a stainless steel metal gauze having a mesh size of 850 µm, and was subjected to hot air drying at 190° C. for 30 minutes. Then, a dried polymer (1) obtained through the drying operation was crushed with use of a roll mill (WML-type roll crusher; manufactured by Inoguchi Giken Ltd.), and was then classified with use of JIS standard sieves having respective mesh sizes of 710 µm and 175 µm.

By the above series of operations, a water-absorbing resin powder (1) ground to have an uneven shape was obtained. Table 1 shows physical properties of the water-absorbing resin powder (1) thus obtained.

Then, with 100 g of the water-absorbing resin powder (1) obtained, a surface crosslinking agent solution containing 0.4 g of ethylene carbonate, 0.6 g of propylene glycol, 2.6 g of deionized water, and 0.001 g of polyoxyethylene (20) sorbitane monostearate (manufactured by Kao Corporation) (10 ppm with respect to the water-absorbing resin) was uniformly mixed, so that a mixture (1) was obtained. The mixture (1) was subjected to a heating treatment at 212° C. for 35 minutes. After the heating treatment, the mixture (1) was force-cooled to 60° C., and was crushed until the mixture (1) passed through a JIS standard sieve having a mesh size of 850 µm, so that a surface-crosslinked water-absorbing resin powder (hereinafter referred to as "water-absorbing resin particles") (1) was obtained. Note that the heating treatment was carried out so that CRC of the water-absorbing resin particles (1) were within a range of 26.7 g/g to 27.7 g/g.

To 100 g of the water-absorbing resin particles (1), 1.2 g of a mixed solution containing 1 part by weight of a 27 weight % aqueous aluminum sulfate solution (8 weight % based on aluminum oxide), 0.3 parts by weight of a 60 weight % aqueous sodium lactate solution, and 0.025 parts by weight of 1,2-propylene glycol was added. After the addition, the resultant mixture was Dried with no air flow at 60° C. for 30 minutes. Then, the resultant particles were crushed until the particles passed through a JIS standard sieve having a mesh size of 850 µm. 30 g of the particles thus crushed was added to a glass container having a diameter of 6 cm and a height of 11 cm. Then, 10 g of glass beads having a diameter of 6 mm was added. Then, the glass container was attached to a paint shaker (manufactured by Toyo Seiki Seisaku-sho, Ltd., product No. 488, the details of the device is disclosed in Japanese Patent Application Publication, Tokukaihei, No. 9-235378). Then, the glass container was shook at 800 cycle/min (CPM) for 10 minutes.

After 10 minutes of shaking, the glass beads were removed with use of a JIS standard sieve having a mesh size of 2 mm, so that a particulate water-absorbing agent (1) was obtained.

The following values of the particulate water-absorbing agent (1) thus obtained were measured: CRC, AAP, FSR, Vortex, SFC, a water-soluble component amount, a weight average molecular weight of the water-soluble component, a molecular weight distribution of the water-soluble component, a weight average molecular weight after a hydrolysis treatment, a molecular weight distribution after the hydrolysis treatment, and a branching density after the hydrolysis treatment. Further, EXI (=CRC/Ln (water-soluble component amount)) was also calculated. Tables 2 and 3 show the results.

Example 2

A water-absorbing resin powder (2) ground to have an uneven shape and a particulate water-absorbing agent (2) were obtained as in Example 1 except that the temperature of the aqueous monomer solution when the 4.5 weight % aqueous sodium persulfate solution was to be added was changed to 79° C. and that the pressure inside the case was changed to 70 kPa. Table 1 shows physical properties of the water-absorbing resin powder (2) thus obtained.

Tables 2 and 3 show physical properties of the particulate water-absorbing agent (2) thus obtained.

Example 3

A water-absorbing resin powder (3) ground to have an uneven shape and a particulate water-absorbing agent (3) were obtained as in Example 1 except that the temperature of the solution (A) when the 48.5 weight % aqueous sodium hydroxide solution was to be added was changed to 50° C., that the temperature of the aqueous monomer solution when the 4.5 weight % aqueous sodium persulfate solution was to be added was changed to 81.5° C., and that the pressure inside the case was changed to 80 kPa. Table 1 shows physical properties of the water-absorbing resin powder (3) thus obtained. Tables 2 and 3 show physical properties of the particulate water-absorbing agent (3) thus obtained.

Example 4

A water-absorbing resin powder (4) ground to have an uneven shape and a particulate water-absorbing agent (4) were obtained as in Example 1 except that the temperature of the aqueous monomer solution when the 4.5 weight % aqueous sodium persulfate solution was to be added was changed to 78.5° C. and that the pressure inside the case was changed to 90 kPa. Table 1 shows physical properties of the water-absorbing resin powder (4) thus obtained. Tables 2 and 3 show physical properties of the particulate water-absorbing agent (4) thus obtained.

Example 5

A water-absorbing resin powder (5) ground to have an uneven shape and a particulate water-absorbing agent (5) were obtained as in Example 1 except that the temperature of the aqueous monomer solution when the 4.5 weight % aqueous sodium persulfate solution was to be added was changed to 78.5° C. and that the pressure inside the case was changed to 72 kPa. Table 1 shows physical properties of the water-absorbing resin powder (5) thus obtained. Tables 2 and 3 show physical properties of the particulate water-absorbing agent (5) thus obtained.

Comparative Example 1

A comparative water-absorbing resin powder (1) ground to have an uneven shape and a comparative particulate water-absorbing agent (1) were obtained as in Example 1 except that the pressure inside the case was changed to normal pressure (101.3 kPa). Table 1 shows physical properties of the comparative water-absorbing resin powder (1) thus obtained. Tables 2 and 3 show physical properties of the comparative particulate water-absorbing agent (1) thus obtained.

Comparative Example 2

A comparative water-absorbing resin powder (2) ground to have an uneven shape and a comparative particulate water-absorbing agent (2) were obtained as in Comparative Example 1 except that the temperature of the solution (A) when the 48.5 weight % aqueous sodium hydroxide solution was to be added was changed to 50° C. and that the temperature of the aqueous monomer solution when the 4.5 weight % aqueous sodium persulfate solution was to be added was changed to 84.5° C. Table 1 shows physical properties of the comparative water-absorbing resin powder (2) thus obtained. Tables 2 and 3 show physical properties of the comparative particulate water-absorbing agent (2) thus obtained.

Comparative Example 3

A comparative water-absorbing resin powder (3) ground to have an uneven shape and a comparative particulate water-absorbing agent (3) were obtained as in Comparative Example 1 except that the temperature of the aqueous monomer solution when the 4.5 weight % aqueous sodium persulfate solution was to be added was changed to 73° C. Table 1 shows physical properties of the comparative water-absorbing resin powder (3) thus obtained. Tables 2 and 3 show physical properties of the comparative particulate water-absorbing agent (3) thus obtained.

Comparative Example 4

A water-absorbing resin taken out from a disposable diaper (manufactured by DSG International Ltd.; product name: "BabyLove PlayPants") purchased in Thailand in December, 2012 was used as a comparative particulate water-absorbing agent (4). Tables 2 and 3 show physical properties of the comparative particulate water-absorbing agent (4).

Comparative Example 5

A water-absorbing resin taken out from a disposable diaper (manufactured by SCA; product name: "Drypers DRYPantz") purchased in Thailand in November, 2013 was used as a comparative particulate water-absorbing agent (5). Tables 2 and 3 show physical properties of the comparative particulate water-absorbing agent (5).

Example 6

A solution (B) was prepared by sufficiently mixing 10 g of ion exchange water with 13.23 g of a 48.5 weight % aqueous sodium hydroxide solution. A solution (C) was prepared by sufficiently mixing 15.84 g of acrylic acid with 0.092 g of polyethyleneglycol diacrylate (weight average molecular weight (Mw) 523 Da) (0.080 mol %). A solution (D) was prepared by sufficiently mixing 0.0594 g of potassium persulfate with 5.76 g of ion exchange water.

The solution (B) was placed in a 120-mL polypropylene container having an inner diameter of 50 mm. Then, while the solution (B) was being stirred with use of a magnetic stirrer and the polypropylene container was being cooled in a water bath, the solution (C) was added in small amounts. Further, the solution (D) was added, so that an aqueous monomer solution (2) was obtained. During the process, a cooling temperature was adjusted so that temperatures of the solutions were not higher than 30° C. With use of a deaeration ball having a pore size of 20 µm and a spherical diameter of 10 mm, a nitrogen gas was introduced into the aqueous monomer solution (2) at a flow rate of 2 L/min. for 15 minutes.

Then, to the aqueous monomer solution (2) into which the nitrogen gas has been introduced, 0.0128 g of tetramethylethylene diamine was added. The resultant mixture was stirred for 10 seconds, so that a reaction liquid (2) was obtained.

A polymerizer having an inner space of 1 mm (height)×25 cm (length)×25 cm (width) was prepared by: preparing a mold form through cutting out a piece of 25 cm (length)×25 cm (width) from a center part of a silicon sheet of 1 mm (thickness)×26 cm (length)×26 cm (width); sandwiching the mold form with two glass plates of 5 mm (thickness)×30 cm (length)×30 cm (width); and fixing four corners of the glass plates with use of a clamp. The inside of the polymerizer was filled with a nitrogen gas. Then, the reaction liquid (2) was injected. Then, the polymerizer was allowed to stand still in a dryer at a temperature of 60° C. so that a thickness direction of the polymerizer extended horizontally. Then, heating was started. In so doing, the reaction liquid (2) had a thickness of 1 mm. Approximately 1 hour after the polymerizer was left still in the dryer, fluidity of the reaction liquid (2) decreased. This confirmed that a reaction was proceeding. 6 hours after the heating was started, the polymerizer was taken out, and a crosslinked hydrogel polymer (hereinafter referred to as "hydrogel") (2) was taken out.

The hydrogel (2) thus obtained was subjected to gel-crushing with use of a screw extruder (meat chopper) having specifications below. The screw extruder included a porous plate at a tip thereof. The porous plate had a diameter of 82 mm and a pore size of 8.0 mm. The number of pores of the porous plate was 33. The porous plate had a thickness of 9.5 mm. The gel-crushing was carried out while the hydrogel (2) was being introduced in an amount of approximately 360 g/min and deionized water at 90° C. was being added in an amount of 50 g/min.

The hydrogel (2) subjected to the gel-crushing was spread on a stainless steel metal gauze having a mesh size of 850 μm, and was subjected to hot air drying at 190° C. for 30 minutes. Then, a dried polymer (2) obtained through the drying operation was crushed with use of a roll mill (WML-type roll crusher; manufactured by Inoguchi Giken Ltd.), and was then classified with use of JIS standard sieves having respective mesh sizes of 710 μm and 175 μm.

By the above series of operations, a water-absorbing resin powder (6) ground to have an uneven shape was obtained. Table 1 shows physical properties of the water-absorbing resin powder (6) thus obtained.

Then, with 100 g of the water-absorbing resin powder (6) obtained, a surface crosslinking agent solution containing 0.4 g of ethylene carbonate, 0.6 g of propylene glycol, 2.6 g of deionized water, and 0.001 g of polyoxyethylene (20) sorbitane monostearate (manufactured by Kao Corporation) (10 ppm with respect to the water-absorbing resin) was uniformly mixed, so that a mixture was obtained. The mixture was subjected to a heating treatment at 212° C. for 35 minutes. After the heating treatment, the mixture was force-cooled to 60° C., and was crushed until the mixture passed through a JIS standard sieve having a mesh size of 850 μm, so that a surface-crosslinked water-absorbing resin powder (hereinafter referred to as "water-absorbing resin particles") (6) was obtained. Note that the heating treatment was carried out so that CRC of the water-absorbing resin particles (6) were within a range of 26.7 g/g to 27.7 g/g.

To 100 g of the water-absorbing resin particles (6), 1.2 g of a mixed solution containing 1 part by weight of a 27 weight % aqueous aluminum sulfate solution (8 weight % based on aluminum oxide), 0.3 parts by weight of a 60 weight % aqueous sodium lactate solution, and 0.025 parts by weight of 1,2-propylene glycol was added. After the addition, the resultant mixture was dried with no air flow at 60° C. for 30 minutes. Then, the resultant particles were crushed until the particles passed through a JIS standard sieve having a mesh size of 850 μm. 30 g of the particles thus crushed was added to a glass container having a diameter of 6 cm and a height of 11 cm. Then, 10 g of glass beads having a diameter of 6 mm was added. Then, the glass container was attached to a paint shaker (manufactured by Toyo Seiki Seisaku-sho, Ltd., product No. 488, the details of the device is disclosed in Japanese Patent Application Publication, Tokukaihei, No. 9-235378).

Then, the glass container was shook at 800 cycle/min (CPM) for 10 minutes.

After 10 minutes of shaking, the glass beads were removed with use of a JIS standard sieve having a mesh size of 2 mm, so that a particulate water-absorbing agent (6) was obtained.

The following values of the particulate water-absorbing agent (6) thus obtained were measured: CRC, AAP, FSR, Vortex, SFC, a water-soluble component amount, a weight average molecular weight of the water-soluble component, a molecular weight distribution of the water-soluble component, a weight average molecular weight after the hydrolysis treatment, a molecular weight distribution after the hydrolysis treatment, and a branching density after the hydrolysis treatment. Further, EXI (=CRC/Ln (water-soluble component amount)) was also calculated. Tables 2 and 3 show the results.

Example 7

A water-absorbing resin powder (7) ground to have an uneven shape and a particulate water-absorbing agent (7) were obtained as in Example 1 except that the polyethyleneglycol diacrylate (weight average molecular weight (Mw) 523 Da) was replaced with 0.0667 g of trimethylolpropane triacrylate (0.070 mol % with respect to the acrylic acid). Table 1 shows physical properties of the water-absorbing resin powder (7) thus obtained. Tables 2 and 3 show physical properties of the particulate water-absorbing agent (7) thus obtained.

Comparative Example 61

A comparative water-absorbing resin powder (6) ground to have an uneven shape and a comparative particulate water-absorbing agent (6) were obtained as in Example 6 except that the thickness of the mold form of the polymerizer was changed to 8 mm. Table 1 shows physical properties of the comparative water-absorbing resin powder (6) thus obtained. Tables 2 and 3 show physical properties of the comparative particulate water-absorbing agent (6) thus obtained.

Example 8

A diffusion absorbency period and a post-deterioration diffusion absorbency period were measured with use of the particulate absorbing agent (1) obtained in Example 1. Touching the top sheet after the measurement revealed that there was no slipperiness. Removing the top sheet and observing the inside revealed that the shape of the gel of the water-absorbing resin was maintained. Table 4 shows the measurement results.

Comparative Example 7

A diffusion absorbency period and a post-deterioration diffusion absorbency period were measured with use of the comparative particulate absorbing agent (1) obtained in Comparative Example 1. Touching the top sheet after the measurement revealed that there was slipperiness. Removing the top sheet and observing the inside revealed that the water-absorbing resin deteriorated so as to have a part whose shape was not maintained. Table 4 shows the measurement results.

TABLE 1

|  | Water-absorbing resin powder | CRC g/g | Ext Weight % | Solid content Weight % | D50 μm | σζ | Proportion of particles in case where particle diameter is less than 150 μm Weight % |
|---|---|---|---|---|---|---|---|
| Example 1 | Water-absorbing resin powder (1) | 38.6 | 10.8 | 96.4 | 395 | 0.35 | 1.2 |
| Example 2 | Water-absorbing resin powder (2) | 36.5 | 8.9 | 96.4 | 376 | 0.36 | 1.4 |
| Example 3 | Water-absorbing resin powder (3) | 35.2 | 7.6 | 96.8 | 380 | 0.35 | 1.7 |
| Example 4 | Water-absorbing resin powder (4) | 37.5 | 10.2 | 96.6 | 391 | 0.38 | 1.5 |
| Example 5 | Water-absorbing resin powder (5) | 37.8 | 10.6 | 96.8 | 388 | 0.36 | 1.4 |
| Comparative Example 1 | Comparative water-absorbing resin powder (1) | 39.6 | 15.5 | 96.2 | 371 | 0.39 | 1.4 |
| Comparative Example 2 | Comparative water-absorbing resin powder (2) | 34.8 | 11.2 | 97.0 | 370 | 0.38 | 1.8 |
| Comparative Example 3 | Comparative water-absorbing resin powder (3) | 40.4 | 25.9 | 96.2 | 396 | 0.40 | 1.7 |
| Example 6 | Water-absorbing resin powder (6) | 39.5 | 9.1 | 96.6 | 381 | 0.37 | 1.0 |
| Example 7 | Water-absorbing resin powder (7) | 38.1 | 12.2 | 96.5 | 390 | 0.36 | 1.5 |
| Comparative Example 6 | Comparative water-absorbing resin powder (6) | 42.0 | 13.0 | 96.2 | 380 | 0.38 | 1.0 |

TABLE 2

|  | Particulate water-absorbing agent | CRC g/g | AAP g/g | FSR g/(g·s) | Vortex Seconds | SFC $(10^{-7} \cdot cm^3 \cdot s \cdot g^{-1})$ | Ext Weight % |
|---|---|---|---|---|---|---|---|
| Example 1 | Particulate water-absorbing agent (1) | 26.9 | 23.9 | 0.35 | 33 | 130 | 7.9 |
| Example 2 | Particulate water-absorbing agent (2) | 27.3 | 24.1 | 0.35 | 32 | 132 | 7.8 |
| Example 3 | Particulate water-absorbing agent (3) | 27.3 | 24.2 | 0.38 | 30 | 139 | 7.4 |
| Example 4 | Particulate water-absorbing agent (4) | 27.0 | 23.6 | 0.34 | 35 | 133 | 8.0 |
| Example 5 | Particulate water-absorbing agent (5) | 26.8 | 24.0 | 0.33 | 36 | 137 | 8.6 |
| Comparative Example 1 | Comparative particulate water-absorbing agent (1) | 27.0 | 23.1 | 0.30 | 39 | 95 | 12.0 |
| Comparative Example 2 | Comparative particulate water-absorbing agent (2) | 27.3 | 23.0 | 0.36 | 32 | 90 | 9.5 |
| Comparative Example 3 | Comparative particulate water-absorbing agent (3) | 26.9 | 20.6 | 0.22 | 57 | 60 | 19.0 |
| Comparative Example 4 | Comparative particulate water-absorbing agent (4) | 38.9 | 15.3 | 0.25 | 49 | 1 | 19.1 |
| Comparative Example 5 | Comparative particulate water-absorbing agent (5) | 33.5 | 13.7 | 0.31 | 39 | 0 | 9.1 |
| Example 6 | Particulate water-absorbing agent (6) | 27.5 | 24.5 | 0.29 | 40 | 131 | 7.0 |
| Example 7 | Particulate water-absorbing agent (7) | 27.1 | 21.0 | 0.32 | 37 | 126 | 9.5 |
| Comparative Example 6 | Comparative particulate water-absorbing agent (6) | 27.6 | 23.1 | 0.26 | 45 | 116 | 8.2 |

TABLE 3

|  | Particulate water-absorbing agent | EXI | Mw of water-soluble component ×10⁴ Da | Mw/Mn of water-soluble component | Mw after hydrolysis treatment ×10⁴ Da | Mw/Mn after hydrolysis treatment | Branching density after hydrolysis treatment | Branching degree after hydrolysis treatment |
|---|---|---|---|---|---|---|---|---|
| Example 1 | Particulate water-absorbing agent (1) | 13.0 | 29 | 4.1 | 120 | 2.4 | 0.072 | 1.760 |
| Example 2 | Particulate water-absorbing agent (2) | 13.3 | 32 | 3.2 | 102 | 2.3 | 0.087 | 1.765 |
| Example 3 | Particulate water-absorbing agent (3) | 13.6 | 29 | 4.3 | 60 | 2.2 | 0.044 | 0.589 |

TABLE 3-continued

|  | Particulate water-absorbing agent | EXI | Mw of water-soluble component ×10⁴ Da | Mw/Mn of water-soluble component | Mw after hydrolysis treatment ×10⁴ Da | Mw/Mn after hydrolysis treatment | Branching density after hydrolysis treatment | Branching degree after hydrolysis treatment |
|---|---|---|---|---|---|---|---|---|
| Example 4 | Particulate water-absorbing agent (4) | 13.0 | 30 | 3.3 | 89 | 2.7 | 0.096 | 2.217 |
| Example 5 | Particulate water-absorbing agent (5) | 12.5 | 30 | 4.4 | 80 | 2.3 | 0.056 | 1.020 |
| Comparative Example 1 | Comparative particulate water-absorbing agent (1) | 10.9 | 24 | 5.2 | 263 | 4.9 | 0.296 | 9.986 |
| Comparative Example 2 | Comparative particulate water-absorbing agent (2) | 12.1 | 28 | 4.9 | 42 | 2.5 | 0.023 | 0.245 |
| Comparative Example 3 | Comparative particulate water-absorbing agent (3) | 9.1 | 19 | 6.7 | 105 | 3.1 | 0.321 | 3.846 |
| Comparative Example 4 | Comparative particulate water-absorbing agent (4) | 13.2 | 116 | 4.5 | 129 | 2.5 | 0.138 | 3.082 |
| Comparative Example 5 | Comparative particulate water-absorbing agent (5) | 15.2 | 83 | 6.6 | 76 | 2.4 | 0.021 | 0.340 |
| Example 6 | Particulate water-absorbing agent (6) | 14.1 | 65 | 3.0 | 49 | 2.3 | 0.032 | 0.346 |
| Example 7 | Particulate water-absorbing agent (7) | 12.0 | 28 | 4.5 | 95 | 2.6 | 0.080 | 2.331 |
| Comparative Example 6 | Comparative particulate water-absorbing agent (6) | 13.1 | 60 | 3.7 | 41 | 2.1 | 0.051 | 0.385 |

TABLE 4

|  | Particulate water-absorbing agent |  | First time | Second time | Third time | Total of first time through third time |
|---|---|---|---|---|---|---|
| Example 8 | Particulate water-absorbing agent (1) | Diffusion absorbency period (sec) | 28 | 37 | 67 | 132 |
|  |  | Post-deterioration diffusion absorbency period (sec) | 31 | 42 | 75 | 148 |
| Comparative Example 7 | Comparative particulate water-absorbing agent (2) | Diffusion absorbency period (sec) | 27 | 37 | 70 | 134 |
|  |  | Post-deterioration diffusion absorbency period (sec) | 31 | 45 | 89 | 165 |

SUMMARY

As shown in Table 3, the EXI, the molecular weight distribution of the water-soluble component, the weight average molecular weight after the hydrolysis treatment, and the branching density after the hydrolysis treatment of each of the particulate water-absorbing agents (1) through (7) obtained in Examples 1 through 7 fall within the ranges specified by the present invention. In contrast, the EXI, the molecular weight distribution of the water-soluble component, the weight average molecular weight after the hydrolysis treatment, and the branching density after the hydrolysis treatment of the comparative particulate water-absorbing agent (1) obtained in Comparative Example 1 fall outside the ranges specified by the present invention. The molecular weight distribution of the water-soluble component and the weight average molecular weight after the hydrolysis treatment of the comparative particulate water-absorbing agent (2) obtained in Comparative Example 2 fall outside the ranges specified by the present invention. The EXI, the molecular weight distribution of the water-soluble component, and the branching density after the hydrolysis treatment of the comparative particulate water-absorbing agent (3) obtained in Comparative Example 3 fall outside the ranges specified by the present invention. The branching density after the hydrolysis treatment of the comparative particulate water-absorbing agent (4) obtained in Comparative Example 4 falls outside the range specified by the present invention. The molecular weight distribution of the water-soluble component of the comparative particulate water-absorbing agent (5) obtained in Comparative Example 5 falls outside the ranges specified by the present invention. The weight average molecular weight after the hydrolysis treatment of the comparative particulate water-absorbing agent (6) obtained in Comparative Example 6 falls outside the range specified by the present invention.

That is, a particulate water-absorbing agent having excellent physical properties can be provided in a case where all of the following conditions are satisfied: an EXI is not less than 11.5; a molecular weight distribution of a water-soluble component is 1.0 to 4.8; a weight average molecular weight after 600 mg of a gel obtained by allowing the particulate water-absorbing agent to swell in a 0.9 weight % aqueous sodium chloride solution is subjected to a treatment of standing still in 10 mL of a 0.1 N aqueous sodium hydroxide solution at 80° C. for 3 weeks is 450,000 Da to 1,800,000 Da; and a branching density after the treatment is not more than 0.100.

Example 8 and Comparative Example 7 indicate that in a case where a particulate water-absorbing agent satisfying all of the above conditions is used for an absorbent body, the absorbent body exhibits deterioration resistance and stable water absorption performance (i.e. has excellent urine resistance).

Therefore, in a case where the particulate water-absorbing agent of the present invention is used for an absorbent body, it is possible to provide a high-performance absorbent body which has an excellent property of absorbing a liquid.

INDUSTRIAL APPLICABILITY

The present invention can be applied to water absorbing agents and water retaining agents for various purposes. In particular, the present invention can be suitably used for absorbent articles such as disposable diapers and sanitary napkins.

The invention claimed is:

1. A particulate water-absorbing agent comprising a polyacrylic acid (salt)-based water-absorbing resin as a main component, said particulate water-absorbing agent satisfying (a) through (d) below:
   (a) EXI represented by the following Formula (1) is not less than 11.5:

$$EXI = \text{centrifuge retention capacity}/\text{Ln (water-soluble component amount)} \quad (1),$$

(b) a molecular weight distribution of a water-soluble component is 1.0 to 4.8÷
   (c) a weight average molecular weight after a hydrolysis treatment is 450,000 Da to 1,800,000 Da, and
   (d) a branching density after the hydrolysis treatment is not more than 0.100,
   said hydrolysis treatment being a treatment carried out by allowing said particulate water-absorbing agent to swell in a 0.9 weight% aqueous sodium chloride solution, removing the water-soluble component so as to obtain a gel, and allowing 600 mg of the gel to stand still in 10 mL of a 0.1 N aqueous sodium hydroxide solution at 80° C. for 3 weeks.

2. The particulate water-absorbing agent according to claim 1, wherein
   a weight average molecular weight of the water-soluble component is 200,000 Da to 1,000,000 Da.

3. The particulate water-absorbing agent according to claim 1, wherein
   a fluid retention capacity under pressure is not less than 20 g/g.

4. The particulate water-absorbing agent according to claim 1, wherein
   a saline flow conductivity is not less than $10 \times 10^{-7} \cdot cm^3 \cdot s \cdot g^{-1}$.

5. The particulate water-absorbing agent according to claim 1, wherein
   a water absorption time is not more than 42 seconds.

6. The particulate water-absorbing agent according to claim 1, wherein
   a free swell rate is not less than 0.28 g/(g·s).

7. The particulate water-absorbing agent according to claim 1, wherein
   a branching degree after the hydrolysis treatment is not more than 2.5.

8. The particulate water-absorbing agent according to claim 1, wherein
   said particulate water-absorbing agent is surface-cross-linked with use of a covalent bonding surface-cross-linking agent.

9. The particulate water-absorbing agent according to claim 1, further comprising:
   a polyvalent metal salt.

10. The particulate water-absorbing agent according to claim 1, wherein
    particles having particle diameters of less than 150 μm are contained at a proportion of not more than 5 weight%.

* * * * *